United States Patent [19]

Hashimoto et al.

[11] 4,264,597
[45] Apr. 28, 1981

[54] CEPHALOSPORIN ANALOGUES AND PROCESSES FOR THE PREPARATION THEREOF

[76] Inventors: Masashi Hashimoto, No. 1-6-17, Satsukidai, Nakayma, Takarazuka; Keiji Hemmi, No. 180, Koaza-Kanafuri, Oaza-Yawataso, Yawatacho, Tsuzuki-gun, Kyoto-fu; Matsuhiko Aratani, No. 52, Awaji-shinmachi, Higashiyodogawa-ku, Osaka; Hidekazu Takeno, No. 21, Higashimuki-kitamachi, Nara; Daijiro Hagiwara, No. 110-4, 2-chome, Kindacho, Moriguchi, all of Japan

[21] Appl. No.: 43,706

[22] Filed: May 30, 1979

[30] Foreign Application Priority Data

Jun. 6, 1978 [GB] United Kingdom .............. 26421/78

[51] Int. Cl.³ ................. C07D 498/04; A61K 31/535
[52] U.S. Cl. ............................... 424/248.54; 424/246; 260/239 A; 544/16; 544/92; 548/217
[58] Field of Search .................... 544/16, 92; 424/246, 424/248.54

[56] References Cited

U.S. PATENT DOCUMENTS 4,089,956   5/1978   Buckley et al. ...................... 544/92

OTHER PUBLICATIONS

"Flynn, Cephalosporins and Penicillins, Chemistry and Biology", pp. 273 to 279, Academic Press (1972).
Scartazzini et al., Chem. Abstracts, vol. 80, abst. 83019p (1974) (abst. of Ger. Offen. 2,331,133 issued 1-17-74, p. 263).
Kim et al., Tetrahedron Letters, No. 5, pp. 409 to 412 (1978).
Lednicer et al., The Organic Chemistry of Drug Synthesis, pp. 418–421, John Wiley and Sons, NY (1978).

Primary Examiner—John D. Randolph

[57] ABSTRACT

Compounds of the formula

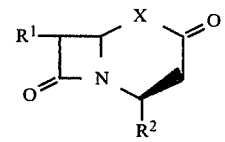

wherein
 X is —O— or —S—;
 $R^1$ is amino or a substituted amino group;
 $R^2$ is carboxy or a protected carboxy group; and the heavy solid line means single or double bond; the compounds are useful in the treatment of infectious diseases particularly fungal infection, in human beings and animals.

32 Claims, No Drawings

CEPHALOSPORIN ANALOGUES AND PROCESSES FOR THE PREPARATION THEREOF

The present invention relates to new cephalosporin analogues and pharmaceutically acceptable salts thereof. More particularly, it relates to new cephalosporin analogues and pharmaceutically acceptable salts thereof which have antimicrobial activities, particularly antifungal activities, and to processes for the preparation thereof, to pharmaceutical composition comprising the same, and to a method of using the same therapeutically for treatment of infectious diseases particularly fungal infection, in human being and animals.

Accordingly, it is one object of the present invention to provide new cephalosporin analogues and pharmaceutically acceptable salts thereof, which are highly active against wide variety of pathogenic microorganisms, particularly fungus.

Another object of the present invention is to provide processes for the preparation of new cephalosporin analogues and pharmaceutically acceptable salts thereof.

A further object of the present invention is to provide pharmaceutical composition comprising, as active ingredients, said cephalosporin analogues and pharmaceutically acceptable salts thereof.

Still further object of the present invention is to provide a method for treatment of infectious diseases caused by pathogenic bacteria, particularly fungus, in human being and animals.

The object cephalosporin analogues of the present invention are novel and can be represented by the following formula (I):

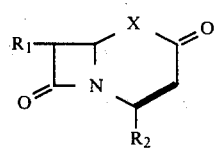
(I)

wherein
X is —O— or —S—;
$R^1$ is amino or a substituted amino group;
$R^2$ is carboxy or a protected carboxy group; and the heavy solid line means single or double bond.

It is to be understood that there may be one or more stereoisomeric pair(s) such as optical and/or geometrical isomers due to asymmetric carbon atom(s) and/or double bond(s) in the molecula of the object compounds (I) and the related compounds (e.g. other object compounds, starting compounds, etc.), of the present invention, and these isomers are also included within the scope of the present invention. The particulars of such isomers will be made clearer in the following explanation.

For example, two configurations may be given due to the 6th position of the fused β-lactam nuclei of the object compounds of the present invention. Accordingly, it is to be noted that the nucleus wherein X is —O— and the heavy solid line is a double bond; the one wherein X is —O— and the heavy solid line is a single bond; the one wherein X is —S— and the heavy solid line is a double bond; and the one wherein X is —S— and the heavy solid line is a single bond; which have the same configurations to those of natural cephalosporin compounds, will be given by the nomenclatures, "1-oxadethia-2-oxo-3-cephem", "1-oxadethia-2-oxocepham", "2-oxo-3-cephem" and "2-oxocepham", respectively. And then, the said nuclei are represented by the formula:

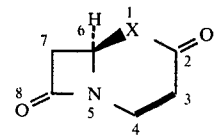

(Note: In the formula, the mark "◀" means β-configuration and the dotted line means α-configuration.), throughout in this specification.

Furthermore, as one skilled in the art can readily appreciate, in case that the heavy solid line is a single bond, the substituent at the 4th position can be in either α or β configuration.

The cephalosporin analogues (I) of the present invention can be prepared by the following processes.

Process 1

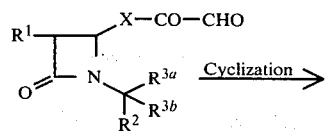
(II)

or its reactive derivatives at the formyl group or a salt thereof

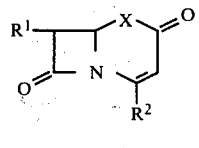
(Ia)

or a salt thereof

Process 2

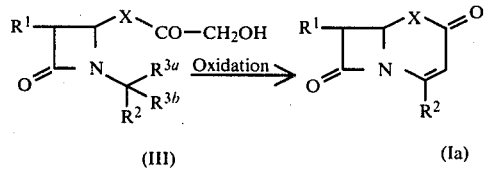
(III)                    (Ia)

or its reactive derivative       or a salt thereof
at the hydroxylmethyl group
or a salt thereof.

Process 3

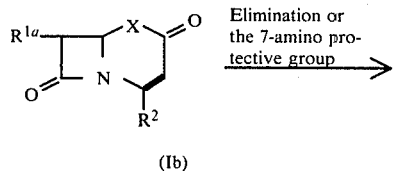
(Ib)

or a salt thereof

Elimination or the 7-amino protective group →

3
-continued

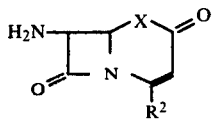

(Ic)

or a salt thereof

Process 4

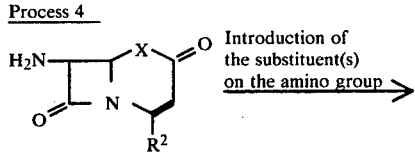

Introduction of the substituent(s) on the amino group →

(Ic)

or its reactive derivatives at the amino group or salt thereof

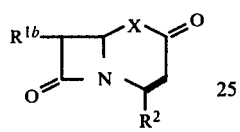

(Id)

or a salt thereof

Process 5

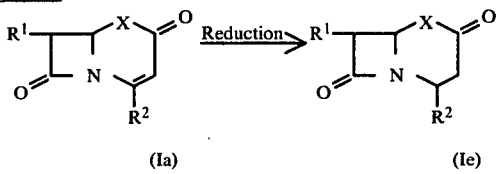

(Ia)                                        (Ie)

or a salt thereof           or a salt thereof

Process 6

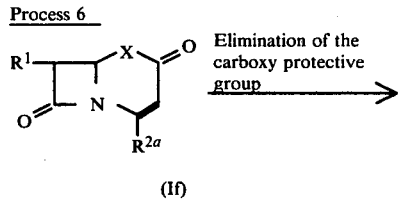

Elimination of the carboxy protective group →

(If)

or a salt thereof

4
-continued

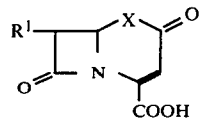

(Ig)

or a salt thereof

Process 7

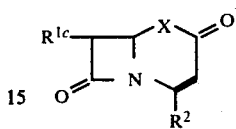

Elimination of the amino protective group →

(Ih)

or a salt thereof

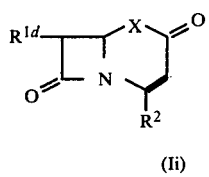

(Ii)

or a salt thereof wherein
$R^1$, $R^2$, X and the heavy solid line are each as defined above;
$R^{1a}$ is a protected amino;
$R^{1b}$ is a substituted amino;
$R^{1c}$ is a substituted amino having a protected amino;
$R^{1d}$ is a substituted amino having an amino;
$R^{2a}$ is a protected carboxy;
$R^3a$ is hydrogen and $R^{3b}$ is a group of the formula:

$$-\overset{O}{\underset{\|}{P}}(OR^4)_2$$

in which $R^4$ is lower alkyl, or
$R^{3a}$ and $R^{3b}$ are linked together to form a group of the formula: $=P(R^5)_3$ in which $R^5$ is lower alkyl, aryl or di(lower)-alkylamino.

The starting compounds (II) and (III) are novel and can be prepared by the processes as illustrated by the following scheme.

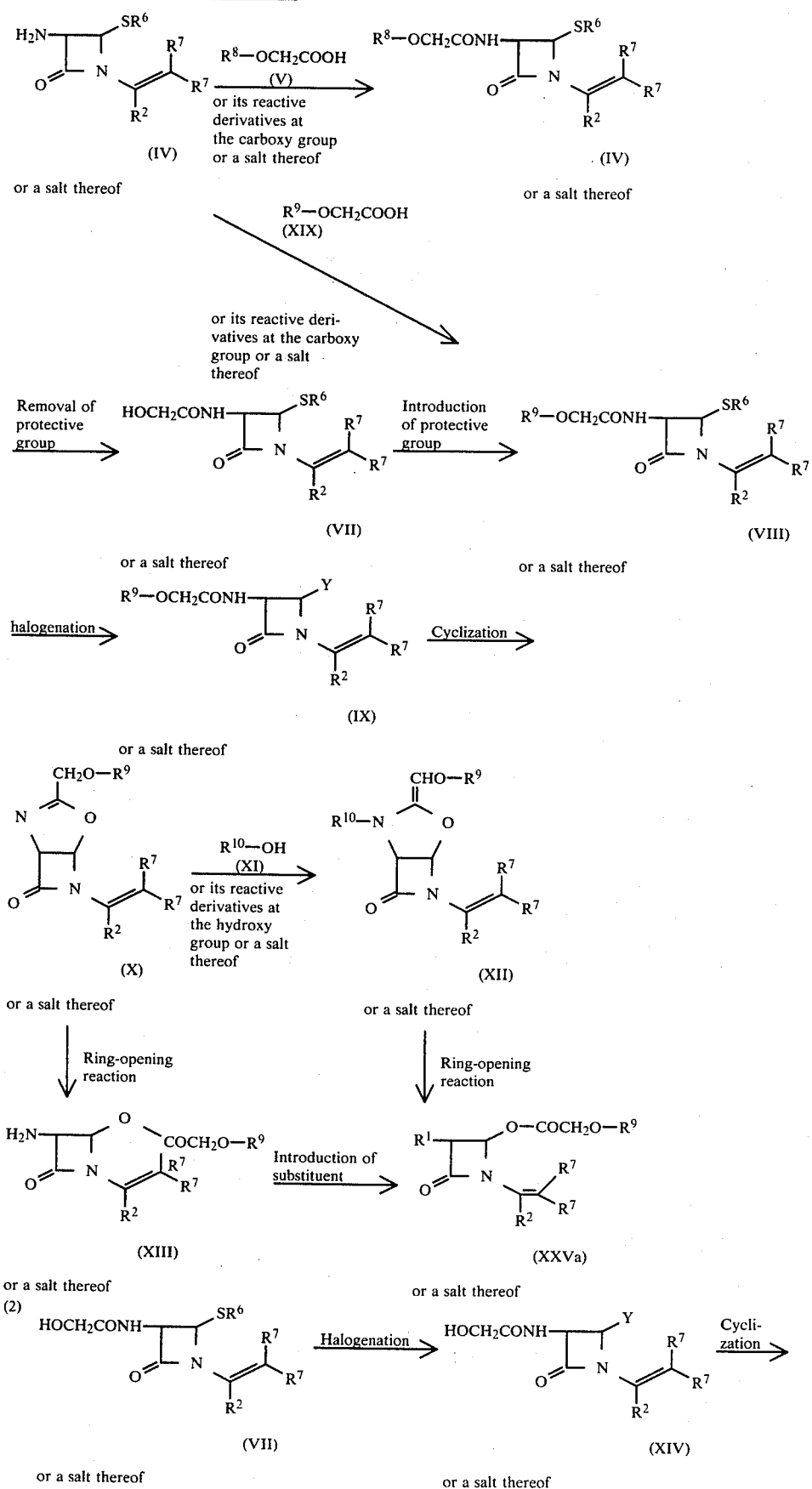

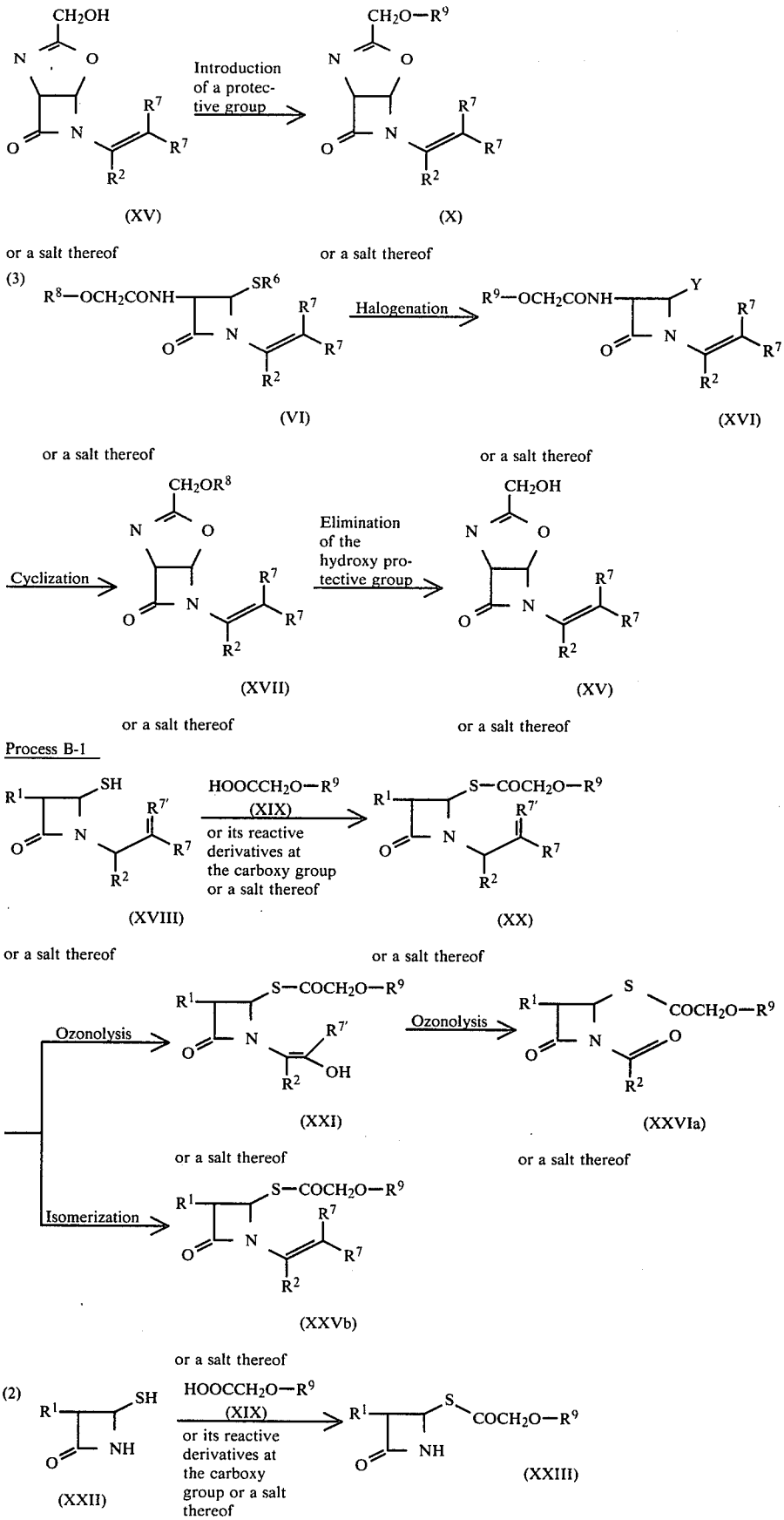

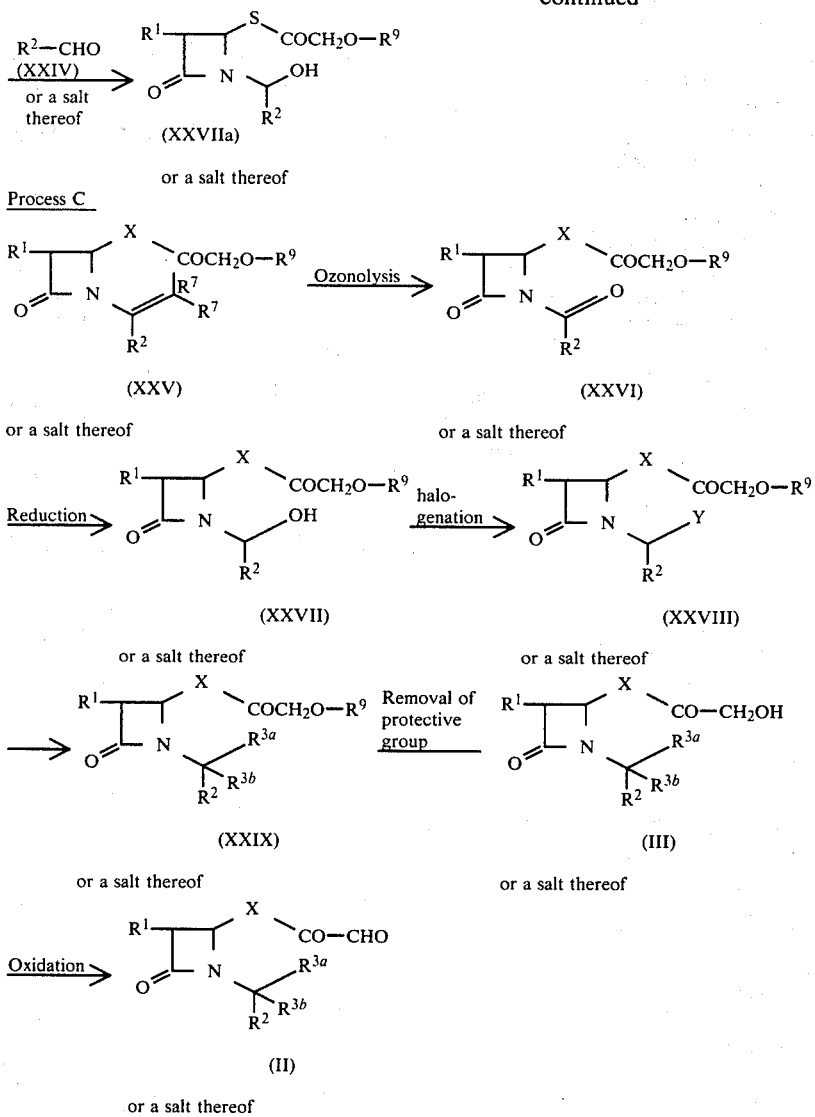

wherein
R$^1$, R$^2$, X, R$^{3a}$ and R$^{3b}$ are each as defined above;
R$^6$ and R$^7$ are each lower alkyl;
R$^{7'}$ is alkylidene;
R$^8$ and R$^9$ are each hydroxy protective group;
Y is halogen; and
R$^{10}$ is a substituent on amino.

Suitable pharmaceutically acceptable salts of the object cephalosporin analogues (I) are conventional nontoxic salts and may include a salt with an inorganic base, for example, a metal salt such as an alkali metal salt (e.g. sodium salt, potassium salt, etc.) and an alkali earth metal salt (e.g. calcium salt, magnesium salt, etc.), ammonium salt, etc., a salt with an organic base, for example, an organic amine salt (e.g. trimethylamine salt, triethylamine salt, pyridine salt, picoline salt, dicyclohexylamine salt, N,N'-dibenzylethylenediamine salt, etc.), etc., an organic acid salt (e.g. maleate, tartrate, methanesulfonate, benzenesulfonate, toluenesulfonate, etc.), an inorganic acid salt (e.g. hydrochloride, hydrobromide, sulfate, phosphate, etc.), or a salt with an amino acid (e.g. arginine, aspartic acid, lysine, glutamic acid, etc.), and the like.

Particulars for the definitions of the present invention are illustrated in details as follows.

The term "lower" is intended to mean 1 to 6 carbon atom(s) and "higher" is intended to mean 7 to 18 carbon atoms respectively unless otherwise provided.

"Substituted amino" may include an amino group substituted with suitable substituent(s) which is conventionally used in cephalosporins and penicillins field as the substituent of amino group at their 7th or 6th position.

Suitable "substituted amino" may include acylamino, and an amino group substituted with a group other than the acyl group, such as ar(lower)alkyl (e.g. benzyl, phenethyl, trityl, etc.) or the like.

Suitable protected carboxy may include esterified carboxy in which said ester may be the ones such as lower alkyl ester (e.g. methyl ester, ethyl ester, propyl, ester, isopropyl ester, butyl ester, isobutyl ester, t-butyl ester, pentyl ester, t-pentyl ester, hexyl ester, 1-cyclopropylethyl ester, etc.); lower alkenyl ester (e.g. vinyl ester, allyl ester etc.); lower alkynyl ester (e.g. ethynyl ester, propynyl ester, etc.); mono(or di or tri)halo(lower)alkyl ester (e.g. 2-iodoethyl ester, 2,2,2-trichloroethyl ester, etc.); lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.); lower alkanesulfonyl(lower)alkyl ester (e.g. 2-mesylethyl ester etc.); ar(lower)alkyl ester, for example, phenyl(lower)alkyl ester which may have one or more suitable substituent(s) (e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-ditertiarybutylbenzyl ester, etc.); aryl ester which may have one or more suitable substituent(s) (e.g. phenyl ester, tolyl ester, tertiarybutylphenyl ester, xylyl ester, mesityl ester, cumenyl ester, etc.), and the like.

Suitable "protected amino" and "protected amino moiety" in the terms "a substituted amino having a protected amino" may include acylamino and an amino group substituted with other conventional protective groups than the acyl groups such as ar(lower)alkyl as aforementioned, and the like.

Suitable "acryl" and "acyl moiety" in the terms "acylamino" as mentioned above may include carbamoyl, aliphatic acyl, aromatic acyl and heterocyclic acyl, wherein said aromatic acyl and heterocyclic acyl are each intended to mean an acyl containing aromatic ring and heterocyclic ring, respectively.

Suitable example of said acyl may be illustrated as follows:

Aliphatic acyl such as lower or higher alkanoyl (e.g. formyl, acetyl, succinyl, hexanoyl, heptanoyl, stearoyl, etc.); lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.); or the like;

Aromatic acyl such as aroyl (e.g. benzoyl, toluoyl, naphthoyl, etc.); ar(lower)alkanoyl (e.g. phenylacetyl, phenylpropionyl, etc.);

aryloxycarbonyl (e.g. phenoxycarbonyl naphthyloxycarbonyl, etc.); aryloxy(lower)alkanoyl (e.g. phenoxyacetyl, phenoxypropionyl, etc.);

arylglyoxyloyl (e.g. phenylglyoxyloyl, naphthylglyoxyloyl, etc.);

ar(lower)alkoxycarbonyl (e.g. benzyloxycarbonyl, diphenylmethoxycarbonyl, etc.); arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);

heterocyclic(lower)alkanoyl (e.g. thienylacetyl, thiazolylacetyl, tetrazolylacetyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl". "heterocyclic(lower)alkanoyl" and "heterocyclicglyoxyloyl" as mentioned above means, in more detail, saturated or unsaturated, monocyclic or polycyclic heterocyclic group containing at least one heteroatom such as an oxygen, sulfur, nitrogen atom and the like.

And, especially preferable heterocyclic group may be heterocyclic group such as unsaturated 3 to 8-membered heteromonocyclic group containing 1 to 4 nitrogen atom(s), for example, pyrrolyl, pyrrolinyl, imidazolyl, pyrazolyl, pyridyl, and its N-oxide, dihydropyridyl, pyrimidyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.), etc.;

saturated 3 to 8-membered heteromonocyclic group containing 1 to 4 nitrogen atom(s), for example, pyrrolidinyl, imidazolidinyl, piperidino, piperazinyl, etc.;

unsaturated condensed heterocyclic group containing 1 to 4 nitrogen atom(s), for example, indolyl, isoindolyl, indolizynyl, benzimidazolyl, quinolyl, isoquinolyl, indazolyl, benzotriazolyl, etc.;

unsaturated 3- to 8-membered heteromonocyclic group containing 1 to 2 oxygen atom(s) and 1 to 3 nitrogen atom(s), for example, oxazolyl, isoxazolyl, oxadiazolyl, (e.g., 1,2,4-oxadiazolyl, 1,3,4-oxadiazolyl, 1,2,5-oxadiazolyl, etc.) etc.;

saturated 3 to 8-membered heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.;

unsaturated 3 to 8-membered heteromonocyclic group containing 1 to 2 sulfur atom(s) and 1 to 3 nitrogen atom(s), for example, thiazolyl, isothiazolyl, thiadiazolyl (e.g., 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered heteromonocyclic group containing 1 to 2 sulfur atom(s) and 1 to 3 nitrogen atom(s), for example, thiazolidinyl, etc.;

unsaturated 3 to 8-membered heteromonocyclic group containing 1 to 2-sulfur atom(s), for example, thienyl, dihydrodithiinyl, dihydrodithiolyl, etc.;

unsaturated condensed heterocyclic group containing 1 to 2 sulfur atom(s) and 1 to 3 nitrogen atom(s), for example, benzothiazolyl, benzothiadiazolyl, etc.;

unsaturated 3 to 8-membered heteromonocyclic group containing an oxygen atom, for example, furyl, etc.;

unsaturated 3 to 8-membered heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety as stated above may have 1 to 10, same or different, suitable substituent(s) such as lower alkyl; lower alkoxy (e.g. methoxy, ethoxy, propoxy, etc.); lower alkylthio (e.g. methylthio, ethylthio, etc.); lower alkylamino (e.g. methylamino, etc.); cyclo(lower)-alkyl (e.g. cyclopentyl, cyclohexyl, etc.); cyclo(lower)-alkenyl (e.g. cyclohexenyl; cyclohexadienyl, etc.); halogen; amino; protected amino; hydroxy; protected hydroxy; cyano; nitro; carboxy; protected carboxy; sulfo; sulfamoyl; imino; oxo; amino(lower)alkyl (e.g. aminomethyl, aminoethyl, etc.); a group of the formula: $=N-OR^{11}$ wherein $R^{11}$ is hydrogen, lower alkyl (e.g., methyl, ethyl, propyl, isopropyl, butyl, pentyl, hexyl, etc.), lower alkenyl (e.g. vinyl, allyl, 2-butenyl, etc.), lower alkynyl (e.g. ethynyl, 2-propynyl, etc.) or cyclo(lower)alkyl (e.g. cyclopropyl, cyclopentyl, cyclohexyl, etc.); or the like.

In this connection, when the acyl moiety has a group of the formula: $=N-OR^{11}$, wherein $R^{11}$ is as defined above, as substituent(s), there are geometrical isomers (syn and anti isomers) due to the presence of double bond. And, for example, the syn isomer means one geometrical isomer having the group of the formula:

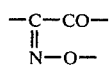

And the corresponding anti isomer means the other geometrical isomer having the group of the formula:

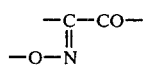

Suitable "lower alkyl" may include one which may be branched, for example, methyl, ethyl, propyl, isopropyl, butyl, isobutyl, t-butyl, pentyl, hexyl and the like, and preferably 1 to 2 carbon atom(s).

Suitable "aryl" may include phenyl, tolyl, xylyl, mesityl, cumenyl, naphthyl and the like.

Suitable "di(lower)alkylamino" may include dimethylamino, diethylamino, dipropylamino, methylethylamino and the like.

Suitable "alkylidene" may include one which may be branches, for example, methylidene, ethylidene, propylidene, isopropylidene, butylidene, isobutylidene, t-butylidene, pentylidene, hexylidene and the like.

Suitable "hydroxy protective group" may include acyl and other conventional protective groups than the acyl groups such as ar(lower)alkyl as aforementioned or the like.

Suitable "halogen" may include chlorine, bromine, fluorine and iodine.

Suitable "substituent or amino" may include acyl, ar(lower)alkyl (e.g. benzyl, phenethyl, trityl, etc.) and the like.

Preferable examples of $R^1$ may be amino or acylamino, more preferably amino, aryloxy(lower)alkanoylamino, most preferably phenoxy(lower)alkanoylamino (e.g. phenoxyacetamido, phenoxypropionamido, etc.);

ar(lower)alkoxycarbonylamino, most preferably phenyl(lower)alkoxycarbonylamino (e.g. benzyloxycarbonylamino, phenethyloxycarbonylamino, etc.);

ar(lower)alkanoylamino which may have lower alkoxyimino, most preferably phenyl(lower)alkanoylamino which may have lower alkoxyimino (e.g. phenylacetamido, phenylpropionamido, 2-methoxyimino-2-phenylacetamido, 2-ethoxyimino-2-phenylacetamido, 2-propoxyimino-2-phenylacetamido, 2-isopropoxyimino-2-phenylacetamido, 2-butoxyimino-2-phenylacetamido, 2-pentyloxyimino-2-phenylacetamido, 2-hexyloxyimino-2-phenylacetamido, etc.);

heterocyclic(lower)alkanoylamino which may have lower alkoxyimino, most preferably thiazolyl(lower)alkanoylamino having lower alkoxyimino and amino or lower alkanoylamino (e.g. 2-methoxyimino-2-(2-aminothiazol-4-yl)acetamido, 2-methoxyimino-2-(2-formamidothiazol-4-yl)acetamido, 2-ethoxyimino-2-(2-aminothiazol-4-yl)acetamido, 2-propoxyimino-2-(2-aminothiazol-4-yl)acetamido, 2-isopropoxyimino-2-(2-aminothiazol-4-yl)acetamido, 2-butoxyimino-2-(2-aminothiazol-4-yl)acetamido, 2-pentyloxyimino-2-(2-aminothiazol-4-yl)acetamido, 2-pentyloxyimino-2-(2-formamidothiazol-4-yl)acetamido, 2-hexyloxyimino-2-(2-aminothiazol-4-yl)acetamido, etc.); and preferable example of $R^2$ may be carboxy or ar(lower)-alkoxycarbonyl, most preferably phenyl(lower)alkoxycarbonyl (e.g. benzyloxycarbonyl, phenethyloxycarbonyl, etc.).

The processes for preparing the object compounds of the present invention are explained in details in the following.

Process 1

The object compound (Ia) or a salt thereof can be prepared by subjecting the compound (II) or its reactive derivative at the formyl group or a salt thereof to cyclization.

Suitable salt of the compound (II) may include an acid addition salt such as an organic acid salt (e.g. acetate, maleate, tartrate, benzenesulfonate, toluenesulfonate, etc.) or an inorganic acid salt (e.g. hydrochloride, hydrobromide, sulfate, phosphate, etc.); a metal salt (e.g. sodium salt, potassium salt, calcium salt, magnesium salt, etc.); ammonium salt; an organic amine salt (e.g. triethylamine salt, dicyclohexylamine salt, etc.), and the like.

Suitable reactive derivative at the formyl group of the compound (II) may include conventional reactive derivative at the formyl group and reactive derivative having equivalent workability to the compound (II) in this reaction. Suitable example of such reactive derivative may include acetal (e.g. dimethyl acetal, diethyl acetal, etc.), hemiacetal, hydrate (diol), thioacetal, hemithioacetal, mono (or di)acylated diol and the like.

In case that the compound (II), in which $R^{3a}$ and $R^{3b}$ are linked together to form a group of the formula =P($R^5$)$_3$ wherein $R^5$ is as defined above, is used as the starting compound, the present reaction is usually carried out in around neutral condition or in the presence of a base as mentioned hereinafter. The reaction is usually carried out in a solvent such as benzene, methylene chloride, dimethylsulfoxide, ethyl acetate, tetrahydrofuran or any other solvent which does not adversely affect the reaction. The reaction temperature is not critical, and the reaction is preferably carried out at ambient temperature or under warming.

In case that the compound (II), in which $R^{3a}$ is hydrogen and $R^{3b}$ is a group of the formula:

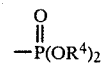

wherein $R^4$ is as defined above, is used as the starting compound, the present reaction is preferably carried out in the presence of a strong base such as alkali metal hydride (e.g. sodium hydride, lithium hydride, etc.), alkaline earth metal hydride (e.g. calcium hydride, etc.), alkali metal t-alkoxide (e.g. sodium t-butoxide, potassium t-butoxide, etc.), ar(lower)alkyl alkali metal (e.g. trityl sodium, trityl lithium, etc.), aryl alkali metal (e.g. phenyl lithium, etc.) or the like. The reaction is usually carried out in a solvent such as benzene, tetrahydrofuran, dioxane or any other solvent which does not adversely affect the reaction. The reaction temperature is not critical, and the reaction is usually carried out at ambient temperature, under warming or heating.

Process 2

The object compound (Ia) a salt thereof can be prepared by oxidizing the compound (III) or its reactive derivative at the hydroxymethyl group or a salt thereof.

Suitable salt of the compound (III) can be referred to the ones exemplified as the salt of the compound (II).

Suitable reactive derivatives at the hydroxymethyl group of the compound (III) may include the compound wherein the hydroxymethyl group of the compound (III) is transformed into methyl group having an acid residue such as halogen (e.g. chlorine, bromine, etc.), arenesulfonyloxy (e.g. p-toluenesulfonyloxy, p-nitrobenzenesulfonyloxy, etc.), haloformyloxy (e.g. chloroformyloxy, etc.) or the like.

Suitable oxidizing agent to be used in this oxidation reaction may include conventional ones which can oxidize hydroxymethyl or reactive derivatives of the hydroxymethyl group to formyl.

In case that the starting compound has 2-hydroxyacetoxy group at the 4th position of azetidinone ring, said oxidizing agent may include (1) an activated dimethylsulfoxide formed by a reaction of dimethylsulfoxide and dicyclohexylcarbodiimide, dimethylsulfoxide and acetic anhydride, dimethylsulfoxide and phosphorus pentoxide, dimethylsulfoxide and sulfur trioxide-pyridine, dimethylsulfoxide and keteneimine, dimethylsulfoxide and chlorine, dimethylsulfoxide and mercuric acetate, dimethylsulfide and N-chlorosuccinimide, dimethylsulfide (or methylphenylsulfide) and chlorine, etc.;

(2) a chrome compound such as chromium trioxide-pyridine, chromium trioxide-sulfuric acid, alkali metal dichlromate (e.g. sodium dichlromate, potassium dichromate, etc.), lower alkyl chromate (e.g. t-butyl chromate, etc.) and the like.

The oxidation using dimethylsulfoxide and dicyclohexylcarbodiimide is preferably carried out in the presence of a proton-donor such as an acid (e.g. phosphoric acid, trifluoroacetic acid, dichloroacetic acid, etc.), a mixture of acid and base (e.g. trifluoroacetic acid-pyridine, phosphoric acid-pyridine, etc.) or the like.

The present oxidation reaction is carried out without or in the presence of an acid or a base, and it is optionally selected according to a kind of oxidizing agent to be used.

The present oxidation is carried out without or with solvent such as benzene, toluene, chloroform, methylene chloride, carbon tetrachloride, diethyl ether, dimethylformamide, dimethylsulfoxide or any other solvent which does not adversely affect the reaction, and the solvent is optionally selected according to a kind of oxidizing agent to be used.

In case that the starting compound of the present oxidation reaction is in a form of a reactive derivatives at the hydroxymethyl group, suitable oxidizing agent may include dimethylsulfoxide and the like. The present oxidation is preferably carried out in the presence of a base (e.g. sodium bicarbonate, triethylamine, etc.).

The reaction temperature of the oxidation reaction of this process is not critical, and the reaction is carried out under cooling, at ambient temperature, under warming or under heating. The reaction temperature is optionally selected, for example, according to a kind of oxidizing agent to be used.

By the present oxidation reaction, there is produced the compound of the formula (II), and said compound (II), without isolation, can be cyclized according to the method mentioned in Process I to give the object compound (Ia).

Process 3

The object compound (Ic) or a salt thereof can be prepared by subjecting the compound (Ib) or a salt thereof to elimination reaction of the 7-amino protective group.

Suitable salt of the compound (Ib) may include a metal salt, ammonium salt, an organic amine salt and the like as aforementioned.

The present elimination reaction is carried out in accordance with a conventional method such as hydrolysis; reduction; elimination using Lewis acid; a method by reacting the compound (Ib) wherein the protective group is acyl group with iminohalogenating agent and then with iminoetherifying agent, and, if necessary, subjecting the resulting compound to hydrolysis; or the like.

The hydrolysis may include a method using an acid or base or hydrazine and the like. These methods may be selected depending on the kind of the protective groups to be eliminated.

Among these methods, hydrolysis using an acid is one of the common and preferable method for eliminating the protective group such as substituted or unsubstituted alkoxycarbonyl (e.g. t-pentyloxycarbonyl, etc.), alkanoyl (e.g. formyl, etc.), cycloalkoxycarbonyl, substituted or unsubstituted aralkoxycarbonyl (e.g. benzyloxycarbonyl, substituted benzyloxycarbonyl, etc.), substituted phenylthio, substituted aralkylidene, substituted alkylidene, substituted cycloalkylidene, or the like. Suitable acid may include an organic or an inorganic acid, for example, formic acid, trifluoroacetic acid, benzenesulfonic acid, p-toluenesulfonic acid, hydrochloric acid and the like, and preferable acid is an acid which can be easily removed from the reaction mixture by a conventional manner such as distillation under reduced pressure, for example, formic acid, trifluoroacetic acid, hydrochloric acid, etc. The acid suitable for the reaction can be selected according to the kind of protective group to be eliminated. When the elimination reaction is conducted with the acid, it can be carried out in the presence or absence of a solvent. Suitable solvent may include an organic solvent, water or a mixed solvent thereof. When trifluoroacetic acid is used, the elimination reaction may be preferably carried out in the presence of anisole.

Among the protective group, the acyl group can be generally eliminated by conventional hydrolysis. In case that the acyl group is halogen substitutedalkoxycarbonyl or 8-quinolyloxycarbonyl, they are eliminated by treating with a heavy metal such as copper, zinc or the like.

The reductive elimination is generally applied for eliminating the protective group, for example, haloalkoxy carbonyl (e.g. trichloroethoxycarbonyl etc.), substituted or unsubstituted aralkoxycarbonyl (e.g. benzyloxycarbonyl, substituted benzyloxycarbonyl etc.), 2-pyridylmethoxycarbonyl, etc. Suitable reduction may include, for example, reduction with an alkali metal borohydride (e.g. sodium borohydride, etc.), catalytic reduction and the like.

The elimination reaction using Lewis acid is carried out substantially in the same manner as described in Process 6.

Suitable iminohalogenating agent used in a method as mentioned above may include phosphorus halide (e.g. phosphorus trichloride, phosphorus pentachloride, phosphorus tribromide, phosphorus pentabromide, etc.), phosphorus oxychloride, thionyl chloride, phosgene and the like.

The reaction temperature is not critical, and the reaction is usually carried out at ambient temperature or under cooling.

Suitable iminoetherifying agent reacted with thus obtained reaction product may include an alcohol, metal alkoxide and the like. Suitable alcohol may include alkanol (e.g. methanol, ethanol, propanol, isopropanol, butanol, t-butanol, etc.) which may be substituted with alkoxy (e.g. methoxy, ethoxy, propoxy, isopropoxy, butoxy, etc.). Suitable metal alkoxide may include alkali metal alkoxide (e.g. sodium alkoxide, potassium alkoxide, etc.), alkaline earth metal alkoxide (e.g. calcium alkoxide, barium alkoxide, etc.) and the like.

The reaction temperature is not critical, and the reaction is usually carried out under cooling or at ambient temperature.

Thus obtained product is, if necessary, subjected to hydrolysis. The hydrolysis can be readily carried out by pouring the reaction mixture obtained above into water, but there may be previously added a hydrophilic solvent (e.g. methanol, ethanol, etc.), a base (e.g. alkali metal bicarbonate, trialkylamine, etc.) or an acid (e.g. diluted hydrochloric acid, acetic acid, etc.) to the water.

The reaction temperature is not critical and may be suitably selected in accordance with the kind of the protective group of the amino group and the elimination method as mentioned above, and the present reaction is preferably carried out under a mild condition such as under cooling, at ambient temperature or slightly elevated temperature.

The present invention includes, within its scope, the case that the protected carboxy is transformed into the free carboxy group according to reaction conditions etc. in the course of the reaction or in post-treatment.

Process 4

The object compound (Id) or a salt thereof can be prepared by subjecting the compound (Ic) or its reactive derivatives at the amino group or a salt thereof to introduction reaction of the substituent(s) on the amino group.

Suitable reactive derivatives at the amino group of the compound (Ic) may include conventional ones such as Schiff's base type imino or its tautomeric enamine type derivatives formed by the reaction of the compound (Ic) with a carbonyl compound (e.g. aldehyde, ketone, etc.), isocyanate; a silyl derivatives formed by the reaction of the compound (Ic) with a silyl compound [e.g. bis(trimethylsilyl)-acetamide, trimethylsilylacetamide, etc.]; a derivatives formed by reaction of the compound (Ic) with phosphorus trichloride or phosgene, or the like.

Suitable salt of the compound (Ic) can be referred to the ones exemplified for the compound (II).

The present introduction reaction of the substituent(s) on the amino group is carried out by reacting the compound (Ic) or its reactive derivatives at the amino group or a salt thereof with an agent which can introduce the substituent(s) on the amino group.

Suitable said agent may include an acylating agent, ar(lower)alkyl halide (e.g. benzyl chloride, trityl chloride, etc.) and the like.

The acylating agent to be used for the present reaction may include one of the formula:

$$R^{12}-OH \quad (XXX)$$

wherein $R^{12}$ is acyl, or its reactive derivatives or a salt thereof.

In case that the compound (XXX) or its reactive derivatives or a salt thereof is used as the agent which introduces substituent(s) on the amino group, an acyl group for $R^{12}$ is introduced on an amino group at the 7th position of the compound (Ic).

Suitable acyl can be referred to the one exemplified hereinbefore.

Suitable reactive derivatives of the compound (XXX) may include an acid halide, an acid anhydride, an activated amide, an activated ester, and the like. The suitable example may be an acid chloride; an acid azide;

a mixed acid anhydride with an acid such as substituted phosphoric acid (e.g. dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkylcarbonic acid, aliphatic carboxylic acid (e.g. pivalic acid, pentanoic acid, isopentanoic acid, 2-ethylbutyric acid or trichloroacetic acid, etc.) or aromatic carboxylic acid (e.g. benzoic acid, etc.);

a symmetrical acid anhydride;

an activated amide with imidazole, 4-substituted imidazole, dimethylpyrazole, triazole or tetrazole; an activated ester [e.g. cyanomethyl ester, methoxymethyl ester, dimethyliminomethyl [$(CH_3)_2N^+=CH-$] ester, vinyl ester, propargyl ester, p-nitrophenyl ester, 2,4-dinitrophenyl ester, trichlorophenyl ester, pentachlorophenyl ester, mesyl phenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, or an ester with N,N-dimethylhydroxylamine, 1-hydroxy-2-(1H)pyridone, N-hydroxysuccinimide, N-hydroxyphthalimide or 1-hydroxy-6-chloro-1H-benzotriazole, and the like.

These reactive derivatives can be optionally selected from them according to the kind of the compound (XXX) to be used.

The salts of the compound (XXX) may be salts with an inorganic base such as an alkali metal salts (e.g. sodium or potassium salt) or an alkaline earth metal salt (e.g. calcium or magnesium salt), a salt with an organic base such as trimethylamine, triethylamine, dicyclohexylamine or the like.

The reaction of the compound (Ic) with the compound (XXX) is usually carried out in a conventional solvent such as water, acetone, dioxane, acetonitrile, chloroform, methylene chloride, ethylene chloride, tetrahydrofuran, ethyl acetate, N,N-dimethylformamide, pyridine or any other organic solvent which does not adversely influence to the reaction.

Among these solvents, hydrophilic solvents may be used in a mixture with water.

When the compound (XXX) is used in free acid form or its salt form in the reaction, the reaction is preferably carried out in the presence of a conventional condensing agent such as carbodiimide compound (e.g. N,N'-dicyclohexylcarbodiimide, N-cyclohexyl-N'-morpholinoethylcarbodiimide, N-cyclohexyl-N'-(4-diethylaminocyclohexyl)carbodiimide, N,N'-diethylcarbodiimide, N,N'-diisopropylcarbodiimide, N-ethyl-N'-(3-dimethylaminopropyl)carbodiimide, etc.), N,N'-carbonylbis(2-methylimidazole),pentamethyleneketene-N-cyclohexylimine, diphenylketene-N-cyclohexylimine, alkoxyacetylene, 1-alkoxy-1-chloroethylene, trialkyl phosphite, ethyl polyphosphate, isopropyl polyphosphate, phosphorus oxychloride, phosphorus trichloride, thionyl chloride, oxalyl chloride, triphenylphosphine, N-ethylbenzisoxazolium salt, N-ethyl-5-phenyl-isoxazolium-3'-sulfonate, 1-(p-chlorobenzenesulfonyloxy)-6-chloro-1H-benzotriazole, Vismeier reagent [e.g. (chloromethylene)dimethylammonium chloride, a compound formed by the reaction of dimethylformamide with phosphorus oxychloride, etc.] or the like.

The reaction may be also carried out in the presence of an inorganic or an organic base such as an alkali metal bicarbonate, alkali metal carbonate, tri(lower)alkylamine, pyridine, N-(lower)alkylmorphorine, N,N-di(lower)alkylbenzylamine, N,N-di(lower)alkylaniline, or the like.

When the base or the condensing agent is in liquid, it can be used also as a solvent. The reaction temperature is not critical, and the reaction is usually carried out under cooling or at ambient temperature.

In this reaction, there may occur partially or nearly complete isomerization between syn and anti geometry of the compound (XXX) wherein acyl group for $R^{12}$ has a group of the formula: $=N-OR^{11}$ wherein $R^{11}$ is as defined above, in the course of the activation process thereof or the reaction with the compound (Ic), depending on surrounding such as reaction conditions or the like. Generally, such isomerization tends to be equilibrated toward the more stable anti-geometry.

Under such chemical behaviors of the compound (XXX), in case of preparing the syn isomer of the object compound (Id) selectively and preparing it in good yield, it is to be noted that it is essential to use syn isomer of the compound (XXX) as a starting compound and to select the reaction conditions suitable for producing the syn isomer selectively and in good yield. For example, for this purpose, the acylation reaction in this process is more preferably conducted by reacting the compounds (Ic) and (XXX) in the presence of a condensing agent such as Vilsmeier reagent, etc. and in a reaction condition such as around neutral.

Process 5

The object compound (Ie) or a salt thereof can be prepared by reducing the compound (Ia) or a salt thereof.

Suitable salts of the compound (Ia) can be referred to the ones as exemplified for the compound (II).

The present reduction can be carried out, for example, by using a combination of a metal (e.g. zinc, zinc amalgam, e.t.c) and an organic or inorganic acid (e.g. acetic acid, propionic acid, hydrochloric acid, e.t.c); by cataltic hydrogenation in the presence of a conventional metallic catalyst and the like.

The present reduction is usually carried out in a solvent such as acetone, dioxane, acetonitrile, benzene, hexane, chloroform, methylene chloride, ethylene chloride, tetrahydrofuran, ethyl acetate or any other solvents which do not adversely affect the reaction.

The reaction temperature is not critical and the reaction is usually carried out under cooling or at ambient temperature.

In this reduction, there is produced a mixture of α and β isomers at 4th position, and said isomers can be separated by conventional methods such as column chromatography or the like.

Process 6

The object compound (Ig) or a salt thereof can be prepared by subjecting the compound (If) or a salt thereof to elimination reaction of the carboxy protective group.

Suitable salt of the compound (If) can be referred to the acid addition salt exemplified for the compound (II).

In the present elimination reaction, conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the present of an acid.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water or a mixed solvent thereof.

The reaction temperature is not critical, and it may be suitably selected in accordance with the kind of the protective group of the carboxy and the elimination method.

The elimination using Lewis acid is preferable to eliminate substituted or unsubstituted ar(lower)alkyl ester and carried out by reacting the compound (Ia) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof. The reaction temperature is not critical, and the reaction is usually carried out under cooling, at ambient temperature or under warming.

Reduction can be applied preferably for elimination of the protective group such as halo(lower)alkyl ester (e.g. 2-iodoethyl, 2,2,2-trichloroethyl, etc.) or the like. The reduction method applicable for the elimination reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, etc.); and conventional catalytic reduction in the presence of a conventional metallic catalyst.

The present elimination reaction of the carboxy protective group includes, within its scope, the cases that protected amino and/or protected carboxy group in the compound (If) is transformed into free amino and/or carboxy group according to reaction conditions and kinds of the protective groups in the course of the reaction and/or in post-treatment of the reaction.

Process 7

The object compound (Ii) or a salt thereof can be prepared by subjecting the compound (Ih) or a salt thereof to elimination reaction of the protective group of the amino.

Suitable salt of the compound (Ih) can be referred to the ones as exemplified for the compound (II).

The present elimination reaction is carried out substantially in the same manner as illustrated in Process 3.

The present invention includes, within its scope, the case that the protected carboxy is transformed into the free carboxy group according to reaction conditions etc. in the course of the reaction or in post-treatment.

In the aforementioned reactions and/or the post-treating of the reactions of the present invention, the aforementioned geometrical isomer and/or tautomeric isomer may occasionally be transformed into the other geometrical isomer and/or tautomeric isomer and such cases are to be also included in the scope of the present invention.

In case that the object compound (I) has free carboxy group and/or free amino group, it may be transformed into its pharmaceutically acceptable salt as aforementioned by a conventional method.

The processes for preparing the starting compounds of the present invention are explained in detail in the following.

Suitable salts of the compounds (IV), (XI), (XII), (XIII), (XVIII), (XX), (XXI), (XXV), (XXVa), (XXVb), (XXVI), (XXVIa), (XXVII), (XXVIIa), (XXVIII), and (XXIX) can be referred to the ones as exemplified for the compound (II).

Suitable salts of the compounds (V), (VI), (VII), (VIII), (IX), (X), (XI), (XIV), (XV), (XVI), (XVII), (XIX) AND (XXIV) can be referred to the ones as exemplified for the compound (Ib).

Suitable reactive derinatives at the carboxy group of the compounds (V) and (XIX) may include an acid halide, an acid anhydride, an activated amide, an activated ester as mentioned in Process 4 and the like.

Preparation A: (1) processes of (IV)+(V)→(VI) [Process A-1];

(IV)+(XIX)→(VIII) [Process -A-1)] and (XIII)→(XXVa) [Process A-1]

The compounds (VI) and (VIII) or a salt thereof can be prepared by reacting the compound (IV) or a salt thereof with the compound (V) or its reactive derivatives at the carboxy group or a salt thereof and by reacting the compound (IV) or a salt thereof with the compound (XIX) or its reactive derivatives at the carboxy group or a salt thereof, respectively; and the compound (XXVa) or a salt thereof can be prepared by subjecting the compound (XIII) or its reactive derivatives at the amino group or a salt thereof to introduction reaction of the substituent(s) on the amino group.

The present reaction can be carried out substantially in the same method as illustrated in Process 4.

(2) a process of (X)+(XI)→(XII) [Process A-1)]

The compound (XII) or a salt thereof can be prepared by reacting the compound (X) or a salt thereof with the compound (XI) or its reactive derivatives at the hydroxy group or a salt thereof.

Suitable reactive derivatives at the hydroxy group of the compound (XI) wherein $R^{10}$ is acyl, may include the ones as exemplified for reactive derivatives of the compound (XXX). Suitable reactive derivatives at the hydroxy group of the compound (XI) wherein $R^{10}$ is, for example, ar(lower)alkyl, may include the ones wherein the hydroxy group is substituted with an acid residue such as halogen, acyloxy (e.g. benzenesulfonyloxy, tosyloxy, etc.) and the like.

The reaction conditions can be referred to the ones as illustrated in Process 4.

Preparation B: Processes of (VI)→(VII) [Process A-1)]; (XVII)→(XV) [Process A-3)] and (XXIX)→(III) [Process C].

The compounds (VII), (XV) and (III) or a salt thereof can be prepared by subjecting the compounds (VI), (XVII) and (XXIX) or a salt thereof to elimination reaction of the protective group of the hydroxy, respectively.

The present elimination reaction is carried out in accordance with a conventional method such as hydrolysis, reduction, elimination using a Lewis acid or the like. These methods can be referred to the ones as illustrated in Process 6.

Preparation C: Processes of (VII)→(VIII) [Process A-1)] and (XV)→(X) [Process A-2)];

The compounds (VIII) and (X) or salts thereof can be prepared by subjecting the compounds (VII) and (XV) or salts thereof to introduction reaction of the protective group of the hydroxy.

The introduction method depends upon the kind of protective group introduced on the hydroxy. In case that the acyl groups are introduced, the present reaction is carried out according to a similar manner to that of Process 4.

The reaction is usually carried out in a conventional solvent such as methylene chloride or any other solvents which do not adversely affect the reaction.

The reaction temperature is not critical, and the reaction is usually carried out under cooling or at ambient temperature.

Preparation D: Processes of (VIII)→(IX) [Process A-1)]; (VII)→(XIV) [Process A-2)]; and (VI)→(XVI) [Process A-3).

The compounds (IX), (XIV) and (XVI) or salts thereof can be prepared by halogenating the compounds (VIII), (VII) and (VI) or a salt thereof, respectively.

The present invention may be carried out by using halogenating agents such as halogen (e.g., chlorine, bromine, etc.) or the like.

The present reaction is usually carried out in a conventional solvent such as methylene chloride, chloroform or any other solvents which do not adversely affect the reaction.

The reaction temperature is not critical, and the reaction is usually carried out under cooling or at ambient temperature.

Preparation E: Processes of (IX)→(X) [Process A-1)]; (XIV)→(XV) [Process A-2)] and (XVI)→(XVII) [Process A-3)].

The compounds (X), (XV) and (XVII) or salts thereof can be prepared by subjecting the compounds (IX), (XIV) and (XVI) or salts thereof to Cyclization reaction.

The present invention is preferably carried out in the presence of inorganic metal salt such as silver salts (e.g.

silver tetrafluoroborate, silver perchloride, etc.), stannic chloride, zinc chloride or the like.

The present reaction may be carried out in the presence of base such as silver oxide or the like.

The reaction is usually carried out in a solvent such as methylene chloride, toluene, chloroform or any other solvents which do not adversely affect the reaction.

The reaction temperature is not critical, and the reaction is preferably carried out under cooling or at ambient temperature.

Preparation F: Processes of (X)→(XIII) [Process A-1)] and (XII)→(XXVa) [Process A-1)].

The compounds (XIII) and (XXVa) or salts thereof can be prepared by subjecting the compounds (X) and (XII) or salts thereof to ring-opening reaction, respectively.

The present reaction may be carried out in accordance with a conventional method such as hydrolysis, especially by using an acid. Suitable acids may include d-camphorsulfonic acid besides the ones as exemplified in Process 3.

The present reaction is usually carried out in a conventional solvent such as methylene chloride, acetone or any other solvents which do not adversely affect the reaction.

The reaction temperature is not critical, and the reaction is usually carried out under cooling, at ambient temperature or under warming.

Preparation G: Processes of (XVIII)+(XIX)→(XX) [Process B-1)] and (XXII)+(XIX)→(XXIII) [Process B-2)].

The compounds (XX) or a salt thereof and (XXIII) can be prepared by reacting the compounds (XVIII) or a salt thereof and (XXII) with the compounds (XIX) or its reactive derivatives at the carboxy group or a salt thereof, respectively.

The reaction conditions can be referred to the ones as illustrated in Process 4.

Preparation H: A process of (XX)→(XXVb) [Process B-1)]

The compound (XXVb) or a salt thereof can be prepared by isomerizing the compound (XX) or a salt thereof.

The present reaction can be carried out in the presence of bases as exemplified in Process 4.

The present reaction is usually carried out in a conventional solvent such as benzene or any other solvents which do not adversely affect the reaction.

The reaction temperature is not critical and the reaction is usually carried out under cooling or at ambient temperature.

Preparation I: A process of (XXIII)+(XXIV)→(XXVIIa) [Process B-2)]

The compound (XXVIIa) or a salt thereof can be prepared by reacting the compound (XXIII) with the compound (XXIV) or a salt thereof.

The reaction is usually carried out in a conventional solvent such as benzene or any other solvents which do not adversely affect the reaction.

The reaction temperature is not critical and the reaction is usually carried out at ambient temperature or under heating.

Preparation J: Processes of (XX)→(XXI) [Process B-1)]; (XXI)→(XXVIa) [Process B-1)] and (XXV)→(XXVI) [Process C].

The compounds (XXI), (XXVIa) and (XXVI) or salts thereof can be prepared by ozonolysis of the compounds (XX), (XXI) and (XXV) or salts thereof and if necessary, reducing the resulting compound.

The present ozonolysis reaction is carried out by reacting the compounds (XX), (XXI) and (XXV) with ozone.

The present reaction is usually carried out in a solvent such as ethyl acetate, methyl acetate or any other solvents which do not adversely affect the reaction.

The reaction temperature is not critical and the reaction is preferably carried out under cooling or at ambient temperature.

In case that the corresponding ozonide compound is produced in the present reaction, the compounds (XXI), (XXVIa) and (XXVI) or salts thereof can be obtained by further reducing the ozonide compound with a conventional reducing agent such as sodium sulfite, sodium bisulfite, dimethyl sulfide trimethylphosphite or the like.

The present reaction is usually carried out in a solvent such as ethyl acetate or any other solvents which do not adversely affect the reaction.

The reaction temperature is not critical and the reaction is preferably carried out under cooling or at ambient temperature.

Preparation K: A process of (XXVI)→(XXVII) [Process C]

The compound (XXVII) or a salt thereof can be prepared by reducing the compound (XXVI) or a salt thereof.

The present reduction can be carried out by a conventional method which is applied to the reduction of -CO- group to the corresponding —CH(OH)— group, for example, by using a combination of a metal (e.g. zinc, etc.) and an organic or inorganic acid (e.g. acetic acid, propionic acid, hydrochloric acid, etc.), lithium borohydride, sodium borohydride, aluminum amalgam; metal amalgam (e.g., aluminum amalgam, etc.), catalytic hydrogenation or the like.

The present reaction is preferably carried out in a solvent such as methylene chloride, tetrahydrofuran or any other solvents which do not adversely affect the reaction.

The reaction temperature is not critical and the reaction is preferably carried out under cooling at ambient temperature or under warming.

Preparation L: A process of (XXVII)→(XXVIII) [Process C]

The compound (XXVIII) or a salt thereof can be prepared by halogenating the compound (XXVII) or a salt thereof.

The present halogenation can be carried out by using a conventional halogenating agent such as phosphorus trihalide, phosphorus pentahalide, phosphorus oxychloride, thionyl halide and the like.

The present reaction may be carried out in the presence of a base such as lutidine, pyridine and the like.

The reaction is usually carried out in a solvent such as methylene chloride or any other solvents which do not adversely affect the reaction.

The reaction temperature is not critical and the reaction is preferably carried out under cooling, at ambient temperature or under warming.

Preparation M: A process of (XXVIII)→(XXIX) [Process C]

The compound (XXIX) or a salt thereof can be prepared by reacting the compound (XXVIII) or a salt thereof with a compound of the formula:

wherein $R^4$ and $R^5$ are each as defined above.

In case that

is used in the present reaction, the present reaction is preferably carried out in the presence of an base as aforementioned.

The reaction is usually carried out in a solvent such as methylene chloride, benzene or any other solvents which do not adversely affect the reaction.

The reaction temperature is not critical and the reaction is preferably carried out at ambient temperature or under warming.

Preparation N: A process of (III)→(II) [Process C]

The compound (II) or a salt thereof can be prepared by oxidizing the compound (III) or a salt thereof.

The present reaction can be carried out substantially in the same method as illustrated in Process 2.

The object compound (I) of the present invention exhibits high antimicrobial activity and inhibits the growth of a wide variety of microorganisms including fungus.

For therapeutic administration, the cephalosporin analogues according to the present invention are used in the form of pharmaceutical preparation which contain said compounds in admixture with a pharmaceutically acceptable carriers such as an organic or inorganic solid or liquid excipient suitable for oral, parenteral or external administration. The pharmaceutical preparations may be in solid form such as capsule, tablet, dragee, ointment or suppository, or in liquid form such as solution, suspension, or emulsion. If desired, there may be included in the above preparations auxiliary substances, stabilizing agents, wetting or emulsifying agents, buffers and other commonly used additives.

While the dosage of the compounds may vary from and also depend upon the age and condition of the patient, an average single dose of about 50 mg., 100 mg., 250 mg., and 500 mg. of the compounds according to the present invention has proved to be effective for treating of infectious diseases caused by a number of pathogenic bacteria. In general amounts between 1 mg. and about 1000 mg. or even more may be administered per day.

Now, in order to show the utility of the object compound (I), the test data on anti-microbial activity of a representative compound of the present invention are shown below.

Test compound (1) Benzyl 7β-(2-phenoxyacetamido)-2-oxo-3-cephem-4-carboxylate.

(2) Benzyl 7β-(2-phenoxyacetamido)-1-oxodethia-2-oxo-3-cephem-4-carboxylate.

Test method

In vitro antibacterial activity was determined by the two-fold agar-plate dilution method as described below.

One loopful of an overnight culture of each test strain in Trypticase-soy broth ($10^{4-5}$ viable spores per ml) was streaked on heart infusion sugar (HI-agar) containing graded concentrations of antibiotics, and the minimal inhibitory concentration (MIC) was expressed in terms of μg/ml after incubation at 37° C. for 20 hours.

| Test result | | |
|---|---|---|
| | MIC (μg/ml) Test compound | |
| Test Bacteria | (1) | (2) |
| *T. asteroides* | 100 | 200 |

The following examples are given for the purpose of illustrating the present invention:

EXAMPLE 1

Preparation of the starting compound: (a)-(1) Triethylamine (31.2 ml.) was added at −40° C. to a solution of benzyl 2-[2-oxo-3β-amino-4β-(methylthio)azetidin-1-yl]-3-methyl-2-butenoate p-toluenesulfonate (49.2 g.) in methylene chloride (100 ml.), and then a solution of (2-acetoxyacetyl) chloride (15.3 g.) in methylene chloride (10 ml.) was added dropwise thereto over 30 minutes. Methylene chloride (25 ml.) was added thereto and the mixture was stirred for 40 minutes, during which the reaction temperature was gradually elevated to −7° C. Cold water and 1N hydrochloric acid were added to the reaction mixture, and both the aqueous layer and the methylene chloride layer were separated. The aqueous layer was further extracted with methylene chloride. The extract and the methylene chloride layer separated above were combined together, in turn washed with 1N hydrochloric acid, a saturated aqueous solution of sodium bicarbonate and an aqueous solution of sodium chloride, dried over magnesium sulfate and concentrated to give oil of benzyl 2-[2-oxo-3β-(2-acetoxyacetamido)-4β-(methylthio)azetidin-1-yl]-3-methyl-2-butenoate (43.95 g.)

I.R. (CH$_2$Cl$_2$) 3410, 1770, 1720, 1695 cm$^{-1}$

N.M.R. (CDCl$_3$, δ) 1.92 (3H, s), 1.99 (3H, s), 2.12 (3H, s), 2.24 (3H, s), 4.60 (2H, s), 5.04 (1H, d, J=4.5 Hz), 5.08 and 5.28 (2H, ABq, J=12 Hz), 5.47 (1H, dd, J=4.5, 8 Hz), 7.03 (1H, d, J=8 Hz), 7.37 (5H, s)

(a)-(2) 1 N aqueous solution of sodium hydroxide (100 ml.) was added dropwise over 30 minutes at 3° C. to a solution of benzyl 2-[2-oxo-3β-(2-acetoxyacetamido)-4β(methylthio)azetidin-1-yl]-3-methyl-2-butenoate (43.95 g.) in a mixture of acetone (260 ml.) and water (100 ml.). After stirring for 10 minutes at the same temperature, the reaction mixture was adjusted to pH 7 with 1 N hydrochloric acid and acetone was distilled off therefrom under reduced pressure. The mixture was extracted twice with ethyl acetate (250 ml. and 50 ml.). The extracts were washed with a saturated aqueous solution of sodium bicarbonate and an aqueous solution of sodium chloride, dried over magnesium sulfate and concentrated to give oil (38.8 g.). The oil was subjected to column chromatography on silica gel (500 g.). The column was in turn eluted with benzene (500 ml.×4), a mixture of benzene and acetone (17:3) and a mixture of benzene and acetone (4:1).

Firstly, from the fractions of a mixture of benzene and acetone (17:3), the starting compound (6.10 g.) was recovered. And then, from the subsequent fractions, benzyl 2-[2-oxo-3β-(2-hydroxyacetamido)-4β-(methylthio)azetidin-1-yl]-3-methyl-2-butenoate (28.75 g.) was obtained.

I. R. ($CH_2Cl_2$) 3600, 3400, 1770, 1720, 1690 cm$^{-1}$

N.M.R. ($CDCl_3$, δ) 1.92 (3H, s), 2.03 (3H, s), 2.24 (3H, s), 4.12 (2H, s), 4.35 (1H, broad s), 5.14 (1H, d, J=4.5 Hz), 5.40 (1H, dd, J=4.5,8 Hz), 5.14 and 5.32 (2H, ABq, J=12 Hz), 7.36 (5H, s), 7.84 (1H, d, J=8 Hz)

(a)-(3) Pyridine (7.35 ml.) was added at −30° C. to a solution of benzyl 2-[2-oxo-3β-(2-hydroxyacetamido)4β-(methylthio)azetidin-1-yl]-3-methyl-2-butenoate (28.65 g.) in methylene chloride (150 ml.), and then a solution of 2,2,2-trichloroethyl chloroformate (17.7 g.) in methylene chloride (10 ml.) was added dropwise thereto at −30° C. over 25 minutes. The reaction temperature was elevated to 0° C., 1 N hydrochloric acid was added thereto and the mixture was shaken. The methylene chloride layer was separated and the aqueous layer was further extracted with methylene chloride. The extracts were combined together, in turn washed with 1 N hydrochloric acid, a saturated aqueous solution of sodium bicarbonate and an aqueous solution of sodium chloride, dried over magnesium sulfate and concentrated to give benzyl 2-[2-oxo-3β-{2-(2,2,2-trichloroethoxy-carbonyloxy)acetamido}-4β-(methylthio)azetidin-1-yl]-3-methyl-2-butenoate (43.30 g.).

I. R. ($CH_2Cl_2$) 3400, 1770, 1710, 1695 cm$^{-1}$

N.M.R. ($CDCl_3$, δ) 1.92 (3H, s), 2.02 (3H, s), 2.27 (3H, s), 4.76 (2H, s), 4.82 (2H, s), 5.44 (1H, dd, J=4.5, 8 Hz), 5.04–5.32 (3H, m), 7.13 (1H, d, J=8 Hz), 7.38 (5H, s)

(a)-(4) A solution of 2-(2,2,2-trichloroethoxy-carbonyloxy)acetyl chloride (114.2 g.) in methylene chloride (100 ml.) was added dropwise to a solution of benzyl 2-[2-oxo-3β-amino-4β-(methylthio)azetidin-1-yl]-3-methyl-2-butenoate p-toluenesulfonate (150 g.) in methylene chloride (1000 ml.) at −40° C. over a period of 30 minutes. The mixture was allowed to warm to 0° C. over a period of 30 minutes. The reaction mixture was washed successively with 1 N hydrochloric acid, ice-water, a saturated aqueous solution of sodium bicarbonate and a saturated aqueous solution of sodium chloride, dried over magnesium sulfate and then evaporated. The residue was chromatographed on silica gel (1 kg.) and eluted successively with benzene and a mixture of benzene and ethyl acetate (5:1 and 3:1) to give an oil of benzyl 2-[2-oxo-3β-{2-(2,2,2-trichloroethoxy-carbonyloxy)acetamido}-4β-(methylthio)azetidin-1-yl]-3-methyl-2-butenoate (174.6 g.).

(a)-(5) A solution of chlorine (6.7 g.) in carbon tetrachloride (78 ml.) was at a time added at −70° C. to a solution of benzyl 2-[2-oxo-3β-{2-(2,2,2-trichloroethoxy-carbonyloxy)acetamido}-4β-(methylthio)azetidin-1-yl]-3-methyl-2-butenoate (43.30 g.) in methylene chloride (220 ml.) and the resulting mixture was stirred for 17 minutes under −50° C. and then stirred for 34 minutes, during which the reaction temperature was gradually elevated to ambient temperature. Nitrogen gas was passed into the reaction mixture under ice-cooling for 40 minutes, and the mixture was concentrated to give oil of benzyl 2-[2-oxo-3β-{2-(2,2,2-trichloroethoxy-carbonyloxy)acetamido}-4α-(chloro)azetidin-1-yl]-3-methyl-2-butenoate (51.5 g.) which contains a small amount of the corresponding 4β-chloro compound. I. R. ($CH_2Cl_2$) 3400, 1780, 1710, 1695 cm$^{-1}$ N.M.R. ($CDCl_3$ δ) 2.05 (3H, s), 2.34 (3H, s), 4.73 (2H, s), 4.84 (2H, s), 5.15 (1H, dd, J=2, 8 Hz), 5.20 (2H, broad s), 5.80 (1H, d, J=2 Hz), 7.3 (1H, d, J=8 Hz), 7.40 (5H, s)

(a)-(6) To a solution of benzyl 2-[2-oxo-3β-{2-(2,2,2-trichloroethoxy-carbonyloxy)acetamido}-4α-(chloro)azetidin-1-yl]-3-methyl-2-butenoate which contains a small amount of the corresponding 4β-chloro compound (2.37 g.) in methylene chloride (20 ml.) were in turn added silver oxide (0.65 g.) and silver tetrafluoroborate (1.10 g.), and the resulting mixture was stirred at −20° C. After stirring for 1 hour, methylene chloride (10 ml.) was added thereto. After stirring for additional 30 minutes, the reaction mixture was allowed to warm to 0° C. and then benzene (30 ml.) and sodium chloride (1 g.) were added thereto. After stirring for 15 minutes, to the mixture was added a saturated aqueous solution of sodium chloride (3 ml.) and the stirring was continued for 10 minutes. The resulting mixture was filtered and the organic layer in the filtrate was in turn washed with a saturated aqueous solution of sodium chloride, water and a saturated aqueous solution of sodium chloride, dried and concentrated to give an oil (2.30 g.). The oil was chromatographed on silica gel (60 g.) and eluted with methylene chloride and then a mixture of methanol and methylene chloride (1:199) to give colorless oil of benzyl 2-[2-{(2,2,2-trichloroethoxy)carbonyloxymethyl}-4-oxo-3a,5a-dihydro-4H-azeto[3,2-d]oxazol-5-yl]-3-methyl-2-butenoate (1.47 g.), which has the following structural formula.

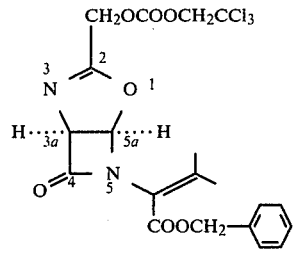

I. R. ($CH_2Cl_2$) 1780, 1720 cm$^{-1}$

N.M.R. ($CDCl_3$, δ) 1.91 (3H, s), 2.25 (3H, s), 4.73 (2H, s), 4.75 (2H, s), 5.11 and 5.22 (2H, ABq, J=13 Hz), 5.2 (1H), 5.98 (1H, d, J=4 Hz), 7.32 (5H, s)

(a)-(7) To a solution of benzyl 2-[2-{(2,2,2-trichloroethoxy)carbonyloxymethyl}-4-oxo-3a,5a-dihydro-4H-azeto[3,2-d]oxazol-5-yl]-3-methyl-2-butenoate (680 mg.) in anhydrous tetrahydrofuran (5 ml.) were added at −78° C. pyridine (0.15 ml.) and 2-phenoxyacetyl chloride (0.21 ml.). The resulting mixture was allowed to warm to ambient temperature with stirring. After stirring for 1⅔ hours, the reaction mixture was concentrated at ambient temperature and the residue was extracted with ethyl acetate. The extract was washed in turn with a diluted hydrochloric acid, a diluted aqueous solution of sodium chloride (twice), a diluted aqueous solution of sodium bicarbonate, a diluted aqueous solution of sodium chloride and a saturated aqueous solution of sodium chloride, dried over magnesium sulfate and concentrated to give an oil of benzyl 2-[2-{(2,2,2-trichloroethoxy)carbonyloxymethylene}-3-(phenoxyacetyl)-4-oxo-2,3,3a,5a-tetrahydro-4H-azeto[3,2-d]- oxazol-5-yl]-3-methyl-2-butenoate (880 mg.), which has the following structural formula.

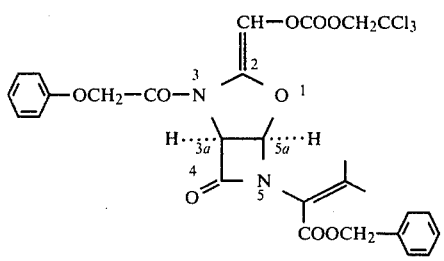

I.R. (CH$_2$Cl$_2$) 1785, 1725, 1700, 1600 cm$^{-1}$

N.M.R. (CDCl$_3$, δ) 1.97 (3H, s), 2.32 (3H, s), 4.82 (2H, s), 4.92 (2H, broad d, J=2 Hz), 5.22 (2H, broad d, J=2 Hz), 5.58 (1H, d, J=4 Hz), 6.15 (1H, d, J=4 Hz), 6.8–7.6 (10H, m), 7.67 (1H, s)

(a)-(8) A mixture of benzyl 2-[2-{2,2,2-trichloroethoxy)carbonyloxymethylene}-3-(2-phenoxyacetyl)-4-oxo-2,3,3a,5a-tetrahydro-4H-azeto[3,2-d]oxazol-5-yl]-3-methyl-2-butenoate (1.30 g.), d-camphorsulfonic acid (23 mg.), methylene chloride (15 ml.) and water (0.054 ml.) was stirred for 30 minutes at ambient temperature. The mixture was extracted with ethyl acetate. The extract was in turn washed with an aqueous solution of sodium bicarbonate, water and a saturated aqueous solution of sodium chloride, dried and concentrated to give an oil (1.37 g.). The oil was chromatographed on silica gel (20 g.) and eluted with a mixture of benzene and acetone (9:1) to give an oil of benzyl 2-[2-oxo-3β-(2-phenoxyacetamido)-4β-{2-(2,2,2-trichloroethoxy-carbonyloxy)acetoxy}azetidin-1-yl]-3-methyl-2-butenoate (1.08 g.).

I.R. (CH$_2$Cl$_2$) 1780, 1765, 1720, 1695 cm$^{-1}$

N.M.R. (CDCl$_3$, δ) 2.08 (3H, s), 2.30 (3H, s), 4.5–4.9 (6H, m), 5.23 (2H, s), 5.38 (1H, dd, J=4,8 Hz), 6.38 (1H, d, J=4 Hz), 6.8–7.6 (11H, m)

(a)-(9) To a solution of benzyl 2-[2-{(2,2,2-trichloroethoxy)carbonyloxymethyl}-4-oxo-3a,5a-dihydro-4H-azeto[3,2-d]oxazol-5-yl]-3-methyl-2-butenoate (15.0 g.) in dry acetone (100 ml.) was added p-toluenesulfonic acid monohydrate (5.81 g.) and the resulting solution was stirred for 20 minutes at 18° C. The reaction mixture was concentrated under reduced pressure to give a semisolid (23 g.). The residue was triturated with diethyl ether (50 ml.) and then petroleum ether (70 ml.) was added thereto. The mixture was cooled, and precipitates were collected by filtration and dried under reduced pressure to give white powder of benzyl 2-[2-oxo-3β-amino-4β-{2-(2,2,2-trichloroethoxy-carbonyloxy)acetoxy}azetidin-1-yl]-3-methyl-2-butenoate p-toluenesulfonate (18.1 g.), m.p. 109°–113° C. (dec.)

I.R. (CH$_2$Cl$_2$) 1785, 1770, 1725 cm$^{-1}$

N.M.R. (d$_6$-DMSO,δ) 2.00 (3H, s), 2.18 (3H, s), 2.33 (3H, s), 4.8–5.1 (3H, m), 5.01 (2H, s), 5.25 (2H, s), 6.47 (1H, d, J=4 Hz), 7.17 and 7.55 (4H, ABq, J=8 Hz), 7.42 (5H, s)

(a)-(10) To a suspension of benzyl 2-[2-oxo-3β-amino-4β-{2-(2,2,2-trichloroethoxy-carbonyloxy)acetoxy}azetidin-1-yl]-3-methyl-2-butenoate p-toluenesulfonate (4.0 g.) in dry methylene chloride (20 ml.) was added 2-phenoxyacetyl chloride (1.03 ml.) under ice-cooling, and to the mixture was added dropwise a solution of pyridine (1 ml.) in dry methylene chloride (4 ml.). The mixture was stirred for 30 minutes at the same temperature, and then evaporated under reduced pressure. The resulting residue was dissolved in ethyl acetate (100 ml.) and in turn washed with dilute hydrochloric acid, water, aqueous solution of sodium bicarbonate and aqueous solution of sodium chloride, and then evaporated to to give oil of benzyl 2-[2-oxo-3β-(2-phenoxyacetamido)-4β-{2-(2,2,2-trichloroethoxy-carbonyloxy)acetoxy}azetidin-1-yl]-3-methyl-2-butenoate (3.9 g.).

(a)-(11) A mixture of Ozone and Oxygen gas was passed at −78° C. into a solution of benzyl 2-[2-oxo-3β-(2-phenoxyacetamido)-4β-[2-(2,2,2- trichloroethoxy-carbonyloxy)acetoxy}azetidin-1-yl]-3-methyl-2-butenoate (338 mg.) in ethyl acetate (6 ml.) until the color of the solution was changed into blue, and the solution was allowed to stand for 5 minutes at −78° C. Then nitrogen gas was passed into the solution at −78° C. to remove an excess ozone gas. The resulting solution was poured into a solution of sodium bisulfite (1.04 g.) and sodium sulfite (0.32 g.) in water (10 ml.) and extracted with ethyl acetate. The extract was in turn washed twice with a diluted aqueous solution of sodium chloride and with a saturated aqueous solution of sodium chloride, dried and concentrated to give a foamy substance (350 mg.), which was crystallized by addition of a mixture of methanol and ether (1:9) to give crystals of benzyl 2-[2-oxo-3β-(2-phenoxyacetamido)-4β-{2-(2,2,2-trichloroethoxy-carbonyloxy)acetoxy}azetidin-1-yl]glyoxylate (240 mg.), m.p. 122°–126° C. (dec.)

I. R. (Nujol) 1830, 1765, 1740, 1720, 1680 cm$^{-1}$

N.M.R. (CDCl$_3$, δ) 4.49 (4H, s), 4.57 (2H, s), 5.26 (2H, s), 5.47 (1H, dd, J=5, 9 Hz), 6.70 (1H, d, J=5 Hz), 6.6–7.5 (11H, m)

(a)-(12) A mixture of benzyl 2-[2-oxo-3β-(2-phenoxyacetamido)-4β-{2-(2,2,2-trichloroethoxy-carbonyloxy)acetoxy}azetidin-1-yl]glyoxylate (395 mg.), zinc powder (300 mg.), propionic acid (0.3 ml.) and methylene chloride (4 ml.) was stirred for 40 minutes at 0° C., for 10 minutes at 13° C. and for 7 minutes at 0° C. The reaction mixture was diluted with cold ethyl acetate (4 ml.) and filtered. The filtrate was in turn washed with a chilled sodium bicarbonate aqueous solution, a diluted aqueous solution of sodium chloride and a saturated aqueous solution of sodium chloride, dried over magnesium sulfate and evaporated to give a foamy substance of benzyl 2-[2-oxo-3β-(2-phenoxyacetamido)-4β-{2-(2,2,2-trichloroethoxycarbonyloxy)acetoxy}azetidin-1-yl]glycolate (a mixture of epimer at 2 position) (370 mg.).

I. R. (CH$_2$Cl$_2$) 1795, 1765, 1695 cm$^{-1}$ (a)-(13) To a solution of benzyl 2-[2-oxo-3β-(2-phenoxyacetamido)-4β-{2-(2,2,2-trichloroethoxy-carbonyloxy)acetoxy}azetidin-1-yl]glycolate (a mixture of epimer at 2 position) (1.26 g.) and 2,6-lutidine (0.35 ml.) in methylene chloride (15 ml.) was added at −30° C. thionyl chloride (0.22 ml.), and the resulting mixture was allowed to warm to 0° C. over 20 minutes and left at 0° C. for 1⅔ hours. The reaction mixture was poured into a chilled diluted aqueous solution of sodium chloride and extracted with ethyl acetate. The extract was successively washed with a diluted aqueous solution of sodium chloride, a diluted aqueous solution of sodium bicarbonate and a saturated aqueous solution of sodium chloride, dried and concentrated to give an oil of benzyl 2-chloro-2-[2-oxo-3β-(2-phenoxyacetamido)-4β-{2-(2,2,2-trichloroethoxy-carbonyloxy)acetoxy}azetidin-1-yl]-acetate (a mixture of epimer at 2 position) (1.31 g.)

I. R. (CH$_2$Cl$_2$) 1805, 1765, 1730, 1700 cm$^{-1}$ (a)-(14) A mixture of the oil (1.31 g.) obtained in the above (10), triphenylphosphine (1.05 g.) and methylene chloride (10 ml.) was allowed to stand for 12 hours at ambient temperature and then heated under reflux for 4.5 hours. The reaction mixture was diluted with methylene chloride, washed with a diluted aqueous solution of sodium bicarbonate, dried over magnesium sulfate and evaporated to give a brown oil. The oil was chromatographed on silica gel (12 g.) and successively eluted with benzene, benzene:ethyl acetate (10:1) and benzene:ethyl acetate (4:1) to give an amorphous solid of benzyl 2-triphenylphosphoranylidene-2-[2-oxo-3β-(2-phenoxyacetamido)-4β-{2-(2,2,2-trichloroethoxy-carbonyloxy)acetoxy}azetidin-1-yl]acetate (986 mg.).

I.R. (CH₂Cl₂) 1765, 1690, 1620 cm⁻¹

(a)–(15) A mixture of benzyl 2-triphenylphosphoranylidene-2-[2-oxo-3β-(2-phenoxyacetamido)-4β-{2-(2,2,2-trichloroethoxy-carbonyloxy)acetoxy}azetidin-1-yl]acetate (915 mg.), zinc powder (750 mg.), acetic acid (0.5 ml.) and methylene chloride (5.0 ml.) was stirred for 4 hours at 15° C. Zinc powder (150 mg.) was further added and the mixture was stirred for 1 hour at 15° C. The reaction mixture was filtered and the filtrate was in turn washed with a saturated aqueous solution of sodium bicarbonate (16 ml.), water, and a saturated aqueous solution of sodium chloride, dried over magnesium sulfate and evaporated to give an oil (780 mg.). The oil was chromatographed on silica gel (5 g.) and successively eluted with benzene, benzene:ethyl acetate (10:1), benzene:ethyl acetate (5:1), benzene-ethyl acetate (2:1) and ethyl acetate to give a foamy substance of benzyl 2-triphenylphosphoranylidene-2-[2-oxo-b 3β-(2-phenoxyacetamido)-4β-(2-hydroxyacetoxy)azetidin-1-yl]acetate (550 mg.).

I. R. (CH₂Cl₂) 1780, 1755, 1690, 1620 cm⁻¹

(b)–(1) To a solution of benzyl 2-[2-oxo-3β-(2-acetoxyacetamido)-4β-(methylthio)azetidin-1-yl]-3-methyl-2-butenoate (4.4 g) in methylene chloride (50 ml) was added a solution of chlorine (1.5 g) in carbon tetrachloride (20 ml) at −78° C. The resulting solution was stirred at −78° C. for 40 minutes and at 0° C. for 20 minutes. The reaction mixture was poured into a cold aqueous solution of sodium bicarbonate and then extracted with methylene chloride (100 ml, 10 ml×2). The extracts were combined, washed successively with water and a saturated aqueous solution of sodium chloride, dried over magnesium sulfate and then evaporated to give an oil of benzyl 2-[2-oxo-3β-(2-acetoxyacetamido)-4α-(chloro)azetidin-1-yl]-3-methyl-2-butenoate (5.5 g).

I.R. (CH₂Cl₂): 1780, 1755, 1700 cm⁻¹ N.M.R. (CDCl₃, δ): 2.00 (3H, s), 2.10 (3H, s), 2.27 (3H, s), 4.54 (2H, s), 5.04 (1H, d, J=8 Hz), 5.18 (2H, s), 5.76 (1H, s), 7.24 (5H, s).

(b)–(2) To a solution of benzyl 2-[2-oxo-3β-(2-acetoxyacetamido)-4α-(chloro)azetidin-1-yl]-3-methyl-2-butenoate (5.5 g) in tetrahydrofuran (40 ml) were added silver oxide (4.6 g) and silver tetrafluoroborate (3.90 g) at −30° C. The resulting mixture was stirred at −20° to −10° C. for 2 hours and 40 minutes and at room temperature for one hour. The reaction mixture was cooled to 0° C. and then benzene (100 ml), an aqueous solution of sodium chloride (20 ml), and an aqueous solution of sodium bicarbonate (20 ml) were added thereto. The mixture was stirred for 20 minutes and filtered through a pad of Celite. The organic layer was separated, washed with a saturated aqueous solution of sodium chloride (×3), dried over magnesium sulfate and then evaporated. The residual oil (5.4 g) was chromatographed on silica gel (120 g) and eluted first with methylene chloride and then with 1.5% solution of methanol in methylene chloride to give an oil of benzyl 2-[2acetoxymethyl-4-oxo-3a,5a-dihydro-4H-azeto[3,2-d]oxazol-5-yl]-3-methyl-2-butenoate (3.30 g), which has the following structural formula.

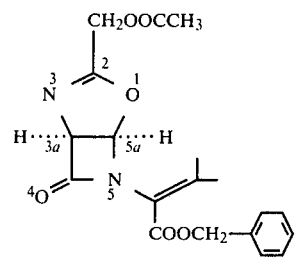

I. R. (CH₂Cl₂): 1780, 1750, 1720 cm⁻¹

N.M.R. (CDCl₃, δ): 1.94 (3H, s), 2.12 (3H, s), 2.19 (3H, s), 4.69 (2H, s), 5.2 (1H), 5.23 (2H, s), 6.01 (1H, d, J=3 Hz), 7.38 (5H, s).

(b)–(3) A mixture of benzyl 2-[2-acetoxymethyl-4-oxo-3a,5a-dihydro-4H-azeto[3,2-d]oxazol-5-yl]-3-methyl-2-butenoate (985 mg) and potassium carbonate (440 mg) in acetone (15 ml) and water (7.5 ml) was heated at 55° C. for 3 hours. The resulting solution was concentrated and to the residue was added ethyl acetate. The ethyl acetate layer was washed successively with water and a saturated aqueous solution of sodium chloride, dried over magnesium sulfate and then evaporated. The residual oil (800 ml) was chromatographed on silica gel (30 g) and eluted first with benzene and then with a mixture of benzene and acetone (3:1) to give benzyl 2-[2-hydroxymethyl-4-oxo-3a,5a-dihydro-4H-azeto[3,2-d]oxazol-5-yl]-3-methyl-2-butenoate (210 mg) and the starting compound (322 mg) was also recovered. The product was identified with that prepared in Example 1 (b)–(5) on a T.L.C. plate.

(b)–(4) To a solution of benzyl 2-[2-oxo-3β-(2-hydroxyacetamido)-4β-(methylthio)azetidin-1-yl]-3-methyl-2-butenoate (1.15 g) in methylene chloride (20 ml) was added a solution of chlorine (440 mg) in carbon tetrachloride (2.5 ml) all at once at −78° C. The resulting mixture was stirred at −78° C. for 40 minutes and at 0° C. for 40 minutes. The reaction mixture was poured into a chilled aqueous solution of sodium bicarbonate (50 ml) and then extracted with methylene chloride. The extracts were washed with a saturated aqueous solution of sodium chloride, dried over magnesium sulfate and then evaporated to give an oil of benzyl 2-[2-oxo-3β-(2-hydroxyacetamido)-4-β-(chloro)azetidin-1-yl]-3-methyl-2-butenoate (1.35 g).

I. R. (CH₂Cl₂): 1780, 1720, 1690 cm⁻¹

(b)–(5) To a mixture of benzyl 2-[2-oxo-3β-(2-hydroxyacetamido)-4β-(chloro)azetidin-1-yl]-3-methyl-2-butenoate (380 mg) and silver oxide (400 mg) in anhydrous tetrahydrofuran (6 ml) was added silver tetrafluoroborate (320 mg) at −40° C. The resulting mixture was stirred at −40° to −30° C. for 30 minutes and then gradually warmed to 0° C. After 70 minutes, benzene (20 ml), an aqueous solution of sodium chloride (3 ml) and a saturated aqueous solution of sodium bicarbonate (1 ml) were added thereto. The reaction mixture was stirred for 5 minutes and then filtered through a pad of Celite. The filtrate was washed successively with water and a saturated aqueous solution of sodium chloride, dried over magnesium sulfate and then evaporated to give an oil (300 mg). The oil (265 mg) was chromatographed on silica gel (7.5 g) and eluted first with methylene chloride and then with 2% solution of methanol in methylene chloride. Fractions containing the object compound were collected and then evaporated to give benzyl 2-[2-hydroxymethyl-4-oxo-3a,5a-dihydro-4H-azeto[3,2-d]oxazol-5-yl]-3-methyl-2-butenoate (96 mg), which has the following structural formula.

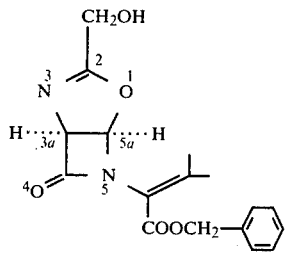

I.R. (CH$_2$Cl$_2$): 1780, 1720, 1655 cm$^{-1}$

N.M.R. (CDCl$_3$, δ): 1.90 (3H, s), 2.27 (3H, s), 3.9 (1H, m), 4.24 (2H, broad s), 5.20 (1H, d, J=3 Hz), 5.23 (2H, s), 6.03 (1H, d, J=3 Hz), 7.39 (5H, s).

(b)-(6) To a solution of benzyl 2-[2-hydroxymethyl-4-oxo-3a,5a-dihydro-4H-azeto[3,2-d]oxazol-5-yl]-3-methyl-2-butenoate (210 mg) and pyridine (64 ml) in methylene chloride (4.5 ml) was added at −35° C. 2,2,2-trichloroethyl chloroformate (96 μl). The resulting mixture was gradually allowed to warm to 0° C. over a period of one hour. The reaction mixture was diluted with ethyl acetate, washed successively with dil. hydrochloric acid, water, a saturated aqueous solution of sodium chloride, a dil. aqueous solution of sodium bicarbonate, a dil. aqueous solution of sodium chloride and a saturated aqueous solution of sodium chloride. The organic layer was dried over magnesium sulfate and evaporated. The residual oil (311 mg) was chromatographed on silica gel (10 g) and eluted with methylene chloride to give an oil of benzyl 2-[2-{(2,2,2-trichloroethoxy)carbonyloxymethyl}-4-oxo-3a,5a-dihydro-4H-azeto[3,2-d]oxazol-5-yl]-3-methyl-2-butenoate (200 mg). The product was identified with that prepared in Example 1 (a)(6) on a T.L.C. plate.

Preparation of the starting compound (c)-(1) To a suspension of benzyl 2-[2-oxo-3β-amino-4β-{2-(2,2,2-trichloroethoxy-carbonyloxy)acetoxy}azetidin-1-yl]-3-methyl-2-butenoate p-toluenesulfonate (18.1 g.) and benzyl chloroformate (3.82 ml.) in methylene chloride (80 ml.) was added dropwise at 0° C. over 15 minutes a solution of pyridine (4.90 ml.) in methylene chloride (10 ml.). The mixture was stirred for 1 hour at 0° C. and concentrated. The residue was dissolved in ethyl acetate (250 ml.), and the solution was in turn washed twice with diluted hydrochloric acid, water, diluted aqueous solution of sodium bicarbonate and a saturated aqueous solution of sodium chloride, dried over magnesium sulfate and concentrated to give an oil (13.2 g.). The oil was chromatographed on silica gel (220 g.) and eluted with benzene and benzene-acetone (20:3) to give an oil of benzyl 2-[2-oxo-3β-benzyloxycarboxamido-4β-{2-(2,2,2-trichloroethoxy-carbonyloxy)acetoxy}azetidin-1-yl]-3-methyl-2-butenoate (13.2 g.).

I.R. (CH$_2$Cl$_2$) 1780, 1760, 1720 cm$^{-1}$

N.M.R. (CDCl$_3$,δ) 2.00 (3H, s), 2.26 (3H, s), 4.60 (2H, s) 4.76 (2H, s), 5.16 (2H, s), 5.20 (2H, s), 5.25 (1H), 5.47 (1H, broad d, J=9 Hz), 6.34 (1H, d, J=4 Hz), 7.37 (10H, s)

(c)-(2) To a solution of benzyl 2-[2-oxo-3β-benzyloxycarboxamido-4β-}2-(2,2,2-trichloroethoxy-carbonyloxy)acetoxy}azetidin-1-yl]-3-methyl-2-butenoate (13.7 g.) in ethyl acetate (260 ml.) was passed at −78° C. a stream of oxygen containing ozone gas for 20 minutes. After the color of the solution became pale blue, an excess ozone gas was removed by bubbling nitrogen gas into the solution at −78° C. for 15 minutes. The mixture was gradually warmed to 0° C. over 40 minutes under a stream of nitrogen. The resulting mixture was poured into a chilled solution of sodium sulfite (10.4 g.) and sodium bisulfite (3.2 g.) in water (100 ml.), and the mixture was shaken. The organic layer was separated, washed with a diluted aqueous solution of sodium chloride (50 ml.) and a saturated aqueous solution of sodium chloride, dried over magnesium sulfate and evaporated to dryness to give an amorphous solid. The residue was crystallized by adding diethyl ether (30 ml.) and the mixture was evaporated to dryness. To the residue was added diisopropyl ether (50 ml.) and the residue was triturated. Crystals were collected by filtration, washed with diisopropyl ether (25 ml.×2) and dried in vacuo to give benzyl 2-[2-oxo-3β-benzyloxycarboxamido-4β-{2-(2,2,2-trichloroethoxy-carbonyloxy)acetoxy}azetidin-1-yl]glyoxylate (12.07 g.), m.p. 118°–121° C. (dec.).

I.R. (Nujol) 1830, 1765, 1735, 1720, 1698 cm$^{-1}$

N.M.R. (CDCl$_3$,δ) 4.56 (2H, broad s), 4.74 (2H, s), 5.10 (2H, broad s), 5.30 (2H, s), 5.2–5.4 (1H, m), 5.68 (1H, d, J=9 Hz), 6.69 (1H, d, J=4 Hz), 7.32 (5H, s), 7.38 (5H, s)

(c)-(3) Zinc powder (995 mg.) was added at 13° C. to a solution of benzyl 2-[2-oxo-3β-benzyloxycarboxamido-4β-{2-(2,2,2-trichloroethoxy-carbonyloxy)acetoxy}azetidin-1-yl]glyoxylate (4.80 g.) and acetic acid (4.8 ml.) in methylene chloride (40 ml.). The resulting mixture was stirred for 3 hours at 13° to 17° C. under a stream of nitrogen, during which an additional zinc powder (400 mg.) was added to the mixture in four portions. The reaction mixture was diluted with ethyl acetate (50 ml.) and filtered. The filtrate was diluted with ethyl acetate (150 ml.), in turn washed with cold water, a diluted aqueous solution of sodium bicarbonate and an aqueous solution of sodium chloride, dried over magnesium sulfate and concentrated to give an oil of benzyl 2-[2-oxo-3β-benzyloxycarboxamido-4β-{2-(2,2,2-trichloroethoxy-carbonyloxy)acetoxy}azetidin-1-yl]-glycolate (a mixture of epimers at 2 position (4.60 g.). The oil was chromatographed on silica gel and eluted with a mixture of benzene and ethyl acetate (4:1) to give a pure compound.

I.R. (CH$_2$Cl$_2$) 1800, 1765, 1740 cm$^{-1}$

N.M.R. (CDCl$_3$,δ) 4.52 and 4.63 (2H, two s), 4.75 (2H, s), 5.12 (2H, s), 5.22 and 5.25 (2H, two s), 5.1–5.6 (2H, m), 5.65–6.0 (1H, m), 6.17 and 6.33 (1H, two d), 7.37 (10H, broad s)

(c)-(4) To a solution of benzyl 2-[2-oxo-3β-benzyloxycarboxamido-4β-{2-(2,2,2-trichloroethoxy-carbonyloxy)acetoxy}azetidin-1-yl]glycolate (9.30 g.) and 2,6-dimethylpyridine (2.68 ml.) in methylene chloride (100 ml.) was added dropwise thionyl chloride (1.68 ml.) over a period of 5 minutes at −30° C. under a nitrogen atmosphere. The resulting mixture was allowed to warm to 0° C. over a period of 20 minutes and then stirred at 0° C. for 1.5 hours. The reaction mixture was poured into ice-water (40 ml.) and thereto was added methylene chloride (50 ml.). After the resulting mixture was shaken, the methylene chloride layer was separated therefrom. The methylene chloride layer was washed successively with ice water and an ice-cooled mixture of a saturated aqueous solution of sodium chloride (50 ml.) and a saturated aqueous solution of sodium bicarbonate (15 ml.), dried over magnesium sulfate and then evaporated to give an oil of benzyl 2-chloro-2-[2-oxo-3β-benzyloxycarboxamido-4β-{2-(2,2,2-trichloroethoxy-carbonyloxy)acetoxy}azetidin-1-yl]acetate (a mixture of epimers at 2 position) (9.50 g.).

I.R. (CH$_2$Cl$_2$)
1805, 1770, 1735 cm$^{-1}$ (c)-(5) A solution of benzyl 2-chloro-2-[2-oxo-3β-benzyloxycarboxamido-4β-{2-(2,2,2-trichloroethoxy-carbonyloxy)acetoxy}azetidin-1-yl]acetate (9.50 g.) and triphenylphosphine (7.9 g.) in methylene chloride (70 ml.) was allowed to stand at room temperature for 13.5 hours under a nitrogen atmosphere and then refluxed under heating for 7 hours also under a nitrogen atmosphere. The reaction mixture was concentrated and poured into ethyl acetate (150 ml.) The mixture was washed successively with an ice-cooled saturated aqueous solution of sodium bicarbonate (30 ml.) and a saturated aqueous solution of sodium chloride, dried over magnesium sulfate and then evaporated. The obtained residual oil (16.4 g.) was subjected to column chromatography on silica gel (200 g.) and eluted successively with benzene and a mixture of benzene and acetone (the mixing ratio: 7/1, 5/1, 4/1, 3/1 and then 2/1). The fractions containing the desired compound were evaporated to give an oil of benzyl 2-triphenylphosphoranylidene-2-[2-oxo-3β-benzyloxycarboxamido-4β-{2-(2,2,2-trichloroethoxy-carbonyloxy)acetoxy}azetidin-1-yl]acetate (6.80 g.).

I.R. (CH$_2$Cl$_2$) 1775, 1770, 1725, 1625 cm$^{-1}$ (c)-(6) To a solution of benzyl 2-triphenylphosphoranylidene-2-[2-oxo-3β-benzyloxycarboxamido-4β-{2-(2,2,2-trichloroethoxy-carbonyloxy)acetoxy}azetidin-1-yl]acetate (6.75 g.) in a mixture of methylene chloride (35 ml.) and acetic acid (3.5 ml.) was added zinc powder (5.5 g.) with stirring at 15° C., and the resulting mixture was stirred at the same temperature for an additional 2 hours and allowed to stand at 0° C. for an hour. The reaction mixture was diluted with ethyl acetate (40 ml.), filtered, and the solid was washed with ethyl acetate. The combined ethyl acetate filtrate and washing was shaked with an ice-cooled saturated aqueous solution of sodium bicarbonate (100 ml.) and then filtered. The organic layer was separated and the remaining aqueous layer was extracted with ethyl acetate (50 ml.). The separated organic layer and the extract were combined together, washed successively with water and a saturated aqueous solution of sodium chloride, dried over magnesium sulfate and then filtered. The filtrate was evaporated to give an amorphous solid (5.35 g.). Thus obtained solid was chromatographed on silica gel (35 g.) and eluted successively with benzene and a mixture of benzene and ethyl acetate (the mixing ratio: 5/1, 2/1 and then 1/1). The fractions containing the desired compounds were evaporated to give an amorphous solid of benzyl 2-triphenylphosphoranylidene-2-[2-oxo-3β-benzyloxycarboxamido-4β-(2-hydroxyacetoxy)azetidin-1-yl]acetate (4.11 g.).

I.R. (CH$_2$Cl$_2$) 1780, 1750, 1725, 1620 cm$^{-1}$

Preparation of the object compound:

(d)-(1) A mixture of benzyl 2-triphenylphoshoranylidene-2-[2-oxo-3β-(2-phenoxyacetamido)-4β-(2-hydroxyacetoxy)azetidin-1-yl]acetate (288 mg.), dimethylsulfoxide (1.4 ml.) and acetic anhydride (1.4 ml.) was stirred for 4 hours at ambient temperature. In the course of the reaction, benzyl 2-triphenylphosphoranylidene-2-[2-oxo-3β-(2-phenoxyacetamido)-4β-(glyoxyloyloxy)azetidin-1-yl]acetate was produced. The reaction mixture was concentrated under reduced pressure at ambient temperature to a volume of 1.5 ml. The residue was poured into a chilled diluted sodium bicarbonate aqueous solution and extracted with a mixture of benzene and ethyl acetate (1:2). The extract was successively washed with a diluted aqueous solution of sodium chloride, water (3 times) and a saturated aqueous solution of sodium chloride, dried over magnesium sulfate and evaporated to give an oil (282 mg.). The oil was chromatographed on silica gel (5 g.) and eluted with benzene and acetone (5:1) to give an amorphous solid of benzyl 7β-(2-phenoxyacetamido)-1-oxadethia-2-oxo-3-cephem-4-carboxylate (134 mg.).

I.R. (CH$_2$Cl$_2$) 1820, 1745, 1700 cm$^{-1}$

N.M.R. (CDCl$_3$, δ) 4.53 (2H, s), 5.33 (2H, s), 5.77 (2H, m), 6.18 (1H, s), 6.7–7.7 (11H, m)

(d)-(2) A solution of benzyl 2-triphenylphosphoranylidene-2-[2-oxo-3β-benzyloxycarboxamido-4β-(2-hydroxyacetoxy)azetidin-1-yl]acetate (1.00 g.) in a mixture of dimethylsulfoxide (4 ml.) and acetic anhydride (4 ml.) was stirred at room temperature for 5 hours and 40 minutes, and then further stirred at 28° to 31° C. for 70 minutes. In the course of the reaction, benzyl 2-triphenylphosphoranylidene-2-[2-oxo-3β-benzyloxycarboxamido-4β-(glyoxyloyloxy)azetidin-1-yl]acetate was produced.

The reaction mixture was concentrated to the volume of about 4 ml under reduced pressure at room temperature. The concentrate was dissolved in a mixture of ethyl acetate and benzene (1:1) (80 ml.), and washed successively with a chilled diluted aqueous solution of sodium bicarbonate, a saturated aqueous solution of sodium chloride, water (3 times) and a saturated aqueous solution of sodium chloride. The solution was dried and then evaporated to give a yellow oil (1.06 g.). Thus obtained oil was chromatographed on silica gel (15 g.) and eluted with a mixture of benzene and ethyl acetate (4:1). The fractions containing the object compound were evaporated to give an oil of benzyl 7β-benzyloxycarboxamido-1-oxadethia-2-oxo-3-cephem-4-carboxylate (370 mg.).

I.R. (CH$_2$Cl$_2$) 1818, 1735 cm$^{-1}$

N.M.R. (acetone-d$_6$,δ) 5.11 (2H, s), 5.35 (2H, s), 5.66 (1H, dd, J=4,9 Hz), 6.06 (1H, d, J=4 Hz), 6.31 (1H, s), 7.1–7.6 (10H, m)

EXAMPLE 2

The following compounds were prepared in the similar manner to that described in Example 1.

(1) Benzyl 7β-[2-pentyloxyimino-2-(2-formamidothiazol-4-yl)acetamido]-1-oxadethia-2-oxo-3-cephem-4-carboxylate (syn isomer).

I.R. (CH$_2$Cl$_2$): 3350, 1810, 1730, 1690 cm$^{-1}$ (2) Benzyl 7β-(2-methoxyimino-2-phenylacetamido)-1-oxadethia-2-oxo-3-cephem-4-carboxylate (syn isomer).

I.R. (CH$_2$Cl$_2$): 3390, 1815, 1740, 1685, 1610 cm$^{-1}$

N.M.R. (CD$_3$)$_2$C=O,δ): 3.95 (3H, s), 5.40 (2H, s), 6.03 (1H, dd, J=4,8 Hz), 6.23 (1H, d, J=4 Hz), 7.33–7.83 (10-11H, m)

EXAMPLE 3

Preparation of the starting compounds (a)-(1) To a suspension of benzyl 2-[2-oxo-3β-(2-phenoxyacetamido)- 4β(mercapto)azetidin-1-yl]-3-methyl-3-butenoate (4.40 g) and 2-(2,2,2-trichloroethoxycarbonyloxy)acetyl chloride (4.02 g) in absolute methylene chloride (22 ml) was added a solution of pyridine (1.03 g) in methylene chloride (5 ml) at −15° to −10° C. with stirring and the stirring was continued for 15 minutes. The reaction mixture was poured into a mixture of ethyl acetate (100 ml) and 2% hydrochloric acid (30 ml). The organic layer was separated, washed successively with water (x2), 5% aqueous solution of sodium bicarbonate (x2) and an aqueous solution of sodium chloride (x3) and then evaporated to give benzyl 2-[2-oxo-3β-(2-phenoxyacetamido)-4β-{2-(2,2,2-trichloroethoxy-carbonyloxy)acetylthio}azetidin-1-yl]-3-methyl-3-butenoate (8.0 g).

I.R. ($CH_2Cl_2$): 1750, 1720, 1700 $cm^{-1}$

N.M.R. ($CDCl_3, \delta$): 1.85 (3H, s), 4.5–5.3 (7H, m), 5.47 (1H, dd, J=5 and 8 Hz), 6.10 (1H, d, J=5 Hz), 6.8–7.5 (11H, m)

(a)-(2) Benzyl 2-[2-Oxo-3β-(2-phenoxyacetamido)-4β-{2-(2,2,2-trichloroethoxy-carbonyloxy)acetylthio}azetidin-1-yl]-3-methyl-3-butenoate (520 mg) was dissolved in ethyl acetate (15 ml) and ozonized under cooling with dry ice-acetone bath until the solution turned pale blue. After the solution was allowed to stand for 10 minutes at the same temperature, nitrogen gas was bubbled through the solution and then the temperature was raised to room temperature. The resulting solution was washed with a solution of sodium sulfite (15 g) and sodium bisulfite (50 g) in water (500 ml) and the washings were extracted with ethyl acetate. The washed organic layer and ethyl acetate extract were combined, washed with a saturated aqueous solution of sodium chloride, dried over magnesium sulfate and then evaporated to give an oil of benzyl 2-[2-oxo-3β-(2-phenoxyacetamido)-4β-{2-(2,2,2-trichloroethoxy-carbonyloxy)acetylthio}azetidin-1-yl]-3-hydroxy-2-butenoate (533 mg).

I. R. ($CH_2Cl_2$): 3400, 1775, 1700, 1660 $cm^{-1}$

N.M.R. ($CLCl_3, \delta$): 2.24 (3H, s), 4.56 (2H, s), 4.77 (2H, s), 4.80 (2H, s), 5.25 (2H, s), 5.21 (1H, d,d, J=5 and 9 Hz), 6.00 (1H, d, J=5 Hz), 6.86–7.50 (10H, m)

(a)-(3) Benzyl 2-[2-Oxo-3β-(2-phenoxyacetamido)-4β-{2-(2,2,2-trichloroethoxy-carbonyloxy)acetylthio}azetidin-1-yl]-3-hydroxy-2-butenoate (244 mg) was dissolved in ethyl acetate (15 ml) and ozonized under cooling with dry ice-acetone until the blue color turned dark. Nitrogen gas was bubbled through the solution and then the temperature was raised to room temperature. The resulting solution was washed with a sodium sulfite-sodium bisulfite solution and then the washing was extracted with ethyl acetate. The washed organic layer and ethyl acetate extract were combined, washed with an aqueous solution of sodium chloride, dried over magnesium sulfate and then evaporated. Diethyl ether and seeds of the object compound were added to the residue and the crystals were collected by filtration washed with diethyl ether and then recrystallized from a mixture of ethyl acetate and diethyl ether to give benzyl 2-[2-oxo-3β-(2-phenoxyacetamido)-4β-{2-(2,2,2-trichloroethoxycarbonyloxy)acetylthio}azetidin-1-yl]glyoxylate (140 mg), mp 130°–134° C.

I. R. (Nujol): 3350, 1820, 1760, 1730, 1720, 1660 $cm^{-1}$

N.M.R. ($CDCl_3, \delta$): 4.56 (2H, s), 4.74 (4H, s), 5.33 (2H, s), 5.50 (1H, dd, J=6.5 and 8.5 Hz), 6.05 (1H, d, J=8.5 Hz), 6.8–7.4 (10H, m).

Elemental Analysis

| | C | H | N | S | Cl |
|---|---|---|---|---|---|
| Calc'd: | 46.35 | 3.27 | 4.32 | 4.95 | 16.42 |
| Found: | 45.95 | 3.16 | 4.35 | 5.27 | 16.46 |

(a)-(4) To a solution of benzyl 2-[2-oxo-3β-(2-phenoxyacetamido)-4β-{2-(2,2,2-trichloroethoxycarbonyloxy)acetylthio}azetidin-1-yl]-3-methyl-3-butenoate (20.5 g) in benzene (200 ml) was added triethylamine (0.85 ml) under ice-cooling. The mixture was stirred for 70 minutes at room temperature. The reaction mixture was washed successively with 1 N hydrochloric acid (60 ml×2) and an aqueous solution of sodium chloride, dried over magnesium sulfate and then evaporated. The residue was subjected to column chromatography on silica gel (120 g), using a mixture of benzene and ethyl acetate (40:1 to 30:1). The fractions containing the object compound were combined and evaporated to give an oil of benzyl 2-[2-oxo-3β-(2-phenoxyacetamido)-4β-{2-(2,2,2-trichloroethoxy-carbonyloxy)acetylthio}azetidin-1-yl]-3-methyl-2-butenoate (6.2 g).

I. R. ($CH_2Cl_2$): 3400, 1770, 1720, 1700 $cm^{-1}$

N.M.R. ($CDCl_3, \delta$): 2.07 (3H, s), 2.25 (3H, s), 4.55 (2H, s), 4.72 (2H, s), 4.75 (2H, s), 5.21 (2H, s), 5.14 (1H, m), 6.01 (1H, d, J=5 Hz), 6.85–7.41 (10H, m).

(a)-(5) Benzyl 2-[2-oxo-3β-(2-phenoxyacetamido)-4β-{2-(2,2,2-trichloroethoxy-carbonyloxy)acetylthio}azetidin-1-yl]-3-methyl-2-butenoate (11.8 g) was dissolved in ethyl acetate (130 ml) and ozonized under cooling with dry ice-acetone bath until the solution turned blue. Nitrogen gas was bubbled through the solution. The resulting solution was washed successively with 50 ml (×2) portions of a solution of sodium bisulfite (50 g) and sodium sulfite (15 g) in water (500 g) and an aqueous solution of sodium chloride, dried over magnesium sulfate and then evaporated to give an oil of benzyl 2-[2-oxo-3β-(2-phenoxyacetamido)-4β-{2-(2,2,2-trichloroethoxy-carbonyloxy)acetylthio}azetidin-1-yl]glyoxylate (10.9 g). This product was identified with that obtained in Example 2 (a)-(3).

(a)-(6) To a suspension of aluminum amalgam (prepared from aluminum powder (20 g) by usual manner) in tetrahydrofuran (300 ml) was added benzyl (2-[2-oxo-3β-(2-phenoxyacetamido)-4β-{2-(2,2,2-trichloroethoxy-carbonyloxy)acetylthio}azetidin-1-yl]-glyoxylate (19.9 g). After the mixture was cooled to 6°–7° C., acetic acid (20 ml) and water (6 ml) were added. The resulting mixture was stirred for 70 minutes at the same temperature and filtered through a pad of Celite. The filtrate was concentrated to half volume and poured into ethyl acetate (700 ml). The mixture was washed with a solution of sodium bicarbonate (44 g) in water (500 ml) and the washing was extracted with ethyl acetate. The organic layers were combined, washed with an aqueous solution of sodium chloride and dried over magnesium sulfate and then evaporated to give a foam of benzyl 2-[2-oxo-3β-(2-phenoxyacetamido)-4β-{2-(2,2,2-trichloroethoxycarbonyloxy)acetylthio}azetidin-1-yl]glycolate (a mixture of epimers at 2 position) (18.8 g).

I. R. ($CH_2Cl_2$): 3480, 3380, 1780, 1740 1690 $cm^{-1}$ (a)-(7) To a mixture of acetic acid (0.5 ml) and methylene chloride (10 ml), were added successively benzyl 2-[2-oxo-3β-(2-phenoxyacetamido)-4β-{2-(2,2,2-trichloroethoxy-carbonyloxy)acetylthio}azetidin-1-yl)glyoxylate (520 mg) and zinc powder (410 mg) with stirring. After the resulting mixture was stirred for an hour at room temperature, insoluble substances were filtered off. The filtrate was diluted with ethyl acetate (50 ml), washed with a dil. aqueous solution of sodium bicarbonate and sodium chloride, dried over magnesium sulfate and then evaporated in vacuo to give benzyl 2-[2-oxo-3β-(2-phenoxyacetamido)-4β-{2-(2,2,2-trichloroethoxy-carbonyloxy)acetylthio}azetidin-1-yl]glycolate (a mixture of epimers at 2 position) (440 mg). This product was identified with that obtained in Example 2(a)–(6).

(a)–(8) A solution of benzyl 2-[2-oxo-3β-(2-phenoxyacetamido)-4β-[2-(2,2,2-trichloroethoxy-carbonyloxy)acetylthio]azetidin-1-yl]glycolate (a mixture of epimers at 2 position) (19.6 g) in methylene chloride (220 ml) was cooled to −40° C. and thereto was added 2,6-lutidine (5.17 g). To the solution was added dropwise a solution of thionyl chloride (5.75 g) in methylene chloride (10 ml) over a period of 20 minutes at the same temperature and then the temperature was gradually raised to −5° C. The mixture containing benzyl 2-chloro-2-[2-oxo-3β-(2-phenoxyacetamido)-4β-[2-(2,2,2-trichloroethoxy-carbonyloxy)acetylthio]azetidin-1-yl]acetate (a mixture of epimers at 2 position) was washed with an aqueous solution of sodium chloride and dried over magnesium sulfate. After addition of triphenylphosphine (15.7 g), the resulting mixture was refluxed for 5.5 hours. The reaction mixture was cooled and then washed with a cold aqueous solution of sodium bicarbonate (×2) and an aqueous solution of sodium chloride, dried over magnesium sulfate and evaporated. The residue was subjected to column chromatography on silica gel (300 g), using a mixture of benzene and ethyl acetate (4:1) was an eluent to give an oil of benzyl 2-triphenylphosphoranylidene-2-[2-oxo-3β-(2-phenoxyacetamido)-4β-{2-(2,2,2-trichloroethoxycarbonyloxy)acetylthio}azetidin-1-yl]acetate (10.65 g).

I. R. (CH$_2$Cl$_2$): 3380, 1760, 1690, 1615 cm$^{-1}$ (a)–(9) To a solution of benzyl 2-triphenylphosphoranylidene-2-[2-oxo-3β-(2-phenoxyacetamido)-4β-{2-(2,2,2-trichloroethoxy-carbonyloxy)acetylthio}azetidin-1-yl]acetate (12.51 g) in methylene chloride (115 ml) were added acetic acid (6.8 ml) and zinc powder (10.0 g) successively under ice cooling and then stirred for an hour at room temperature. After addition of ethyl acetate (400 ml), the reaction mixture was filtered through Celite. The filtrate was washed with a saturated aqueous solution of sodium bicarbonate and an aqueous solution of sodium chloride, dried over magnesium sulfate and then evaporated to give a crude product (10.4 g), which was subjected to column chromatography on silica gel (90 g), using a mixture of benzene and ethyl acetate (3:1) as an eluent to give an oil (5.6 g). This product was crystallized from benzene to give benzyl 2-triphenylphosphoranylidene 2-[2-oxo-3β-(2-phenoxyacetamido)-4β-(2-hydroxyacetylthio)azetidin-1-yl]acetate (2.1 g). mp 128° to 132° C.

I. R. (Nujol): 3300, 3060–3180, 1770, 1680, 1600 cm$^{-1}$

Elemental Analysis:

|  | C | H | N |
|---|---|---|---|
| Calc'd: | 66.84 | 4.91 | 3.90 |
| Found: | 67.16 | 4.96 | 3.66 |

Preparation of the object compound (b) A mixture of benzyl 2-triphenylphosphoranylidene-2-[2-oxo-3β-(2-phenoxyacetamido)-4β-(2-hydroxyacetylthio)azetidin-1-yl]acetate (2.04 g), acetic anhydride (8 ml) and dimethylsulfoxide (8 ml) was stirred for 4 hours and 45 minutes at room temperature. In the course of the reaction, benzyl 2-triphenylphosphoranylidene-2-[2-oxo-3β-(2-phenoxyacetamido)-4β-(glyoxyloylthio)azetidin-1-yl]acetate was produced. After removal of the excess acetic anhydride in vacuo, the resulting solution was poured into ethyl acetate and cold water. The organic layer was separated, washed with water, a diluted aqueous solution of sodium bicarbonate and an aqueous solution of sodium chloride in turn, dried over magnesium sulfate and then evaporated. The residual oil was subjected to column chromatography on silica gel (24 g) and eluted first with benzene and then with a mixture of benzene and ethyl acetate (9:1) to give an amorphous solid, which was crystallized by diethyl ether to give of benzyl 7β-(2-phenoxyacetamido)-2-oxo-3-cephem-4-carboxylate (0.80 g). mp. 127°–128° C.

I. R. (CH$_2$Cl$_2$): 3390, 1805, 1735, 1700, 1655 cm$^{-1}$

N.M.R. (DMSO-d$_6$,δ): 4.63 (2H, s), 5.36 (2H, s), 5.86 (1H, dd, J=5 and 8 Hz), 6.05 (1H, d, J=5 Hz), 6.33 (1H, s), 6.88–7.05, 7.20–7.50 (10H, m), 9.36 (1H, d, J=8 Hz).

Elemental Analysis:

|  | C | H | N | S |
|---|---|---|---|---|
| Calc'd: | 60.26 | 4.13 | 6.39 | 7.31 |
| Found: | 60.63 | 4.12 | 6.29 | 7.08 |

U.V. (Dioxane) λmax 314 (ε=6022), 277 (ε=4196), 270 (ε=3987).

EXAMPLE 4

Preparation of the starting compounds (a)–(1) A mixture of 2-oxo-3β-(2-phenylacetamido)-4β-mercaptoazetidine (4.72 g), 2-(2,2,2-trichloroethoxycarbonyloxy)acetyl chloride (9.38 g) and methylene chloride (25 ml) was cooled to 0° C. and pyridine (2.21 g) was added thereto with stirring and then the stirring was continued for an hour at the same temperature. The reaction mixture was diluted with ethyl acetate (120 ml) and poured into ice-water (120 ml). The organic layer was separated, washed successively with 2% hydrochloric acid (30 ml), water (30 ml), 2% aqueous solution of sodium bicarbonate (30 ml) and water (30 ml), dried over magnesium sulfate and then evaporated in vacuo. The residue was triturated with diethyl ether (150 ml) and the precipitates were collected by filtration, washed with diethyl ether and then dried to give 2-oxo-3β-(2-phenylacetamido)-4β-[2-(2,2,2-trichloroethoxycarbonyloxy)acetylthio]azetidine (7.60 g).

I. R. (CH$_2$Cl$_2$): 3400, 1785, 1770, 1685 cm$^{-1}$ N.M.R. (DMSO-d$_6$+D$_2$O,δ): 3.62 (2H, s), 4.8–5.5 (5H, m), 5.63 (1H, d, J=4.5 Hz), 7.35 (5H, s).

(a)–(2) A solution of 2-oxo-3β-(2-phenylacetamido)-4β-{2-(2,2,2-trichloroethoxy-carbonyloxy)-acetylthio}azetidine (469 mg) and benzyl glyoxylate (1.64 g) in benzene (20 ml) was stirred under reflux for 11 hours with continuous removal of water (Dean-Stark apparatus). The reaction mixture containing benzyl 2-[2-oxo-3β-(2-phenylacetamido)-4β-{2-(2,2,2-trichloroethoxy)-carbonyloxyacethylthio}azetidin 1-yl]glycolate (a mixture of epimers at 2 position). was washed successively with 10% aqueous solution of sodium bisulfite (20 ml×5), and water (×2), dried over magnesium sulfate and then evaporated. To a solution of the residual oil (1.36 g) in absolute methylene chloride (30 ml), 2,6-lutidine (535 mg) was added and then the solution was cooled to 0° C. After addition of thionyl chloride (600 mg) with stirring, the solution was stirred for 45 minutes at 0° C. The reaction mixture containing benzyl 2-chloro-2-[2-oxo-3β-(2-phenylacetamido)-4β-{2-(2,2,2-trichloroethoxy)carbonyloxyacethylthio}azetidin-1-yl]acetate (a mixture of epimers at 2 position) was washed with an aqueous solution of sodium chloride (20 ml×3), dried over magnesium sulfate and then triphenylphosphine (1.40 g) was added thereto. The resulting mixture was refluxed for 10 hours. The reaction mixture was washed successively with 5% aqueous solution of sodium bicarbonate (30 ml) and water (30 ml×2), dried over magnesium sulfate and then evaporated. The residual oil (1.95 g) was subjected to column chromatography on silica gel using a mixture of benzene and ethyl acetate as an eluent to give benzyl 2-triphenylphosphoranylidene-2-[2-oxo-3β-(2-phenylacetamido)-4β-{2-(2,2,2-trichloroethoxycarbonyloxy)acetylthio}azetidin-1-yl]acetate (0.54 g).

I. R. ($CH_2Cl_2$): 1755, 1720, 1670, 1610 $cm^{-1}$ (a)-(3) To a mixture of acetic acid (0.25 ml) and methylene chloride (2.5 ml), benzyl 2-triphenylphosphoranylidene-2-[2-oxo-3β-(2-phenylacetamido)-4β-{2-(2,2,2-trichloroethoxy-carbonyloxy)acetylthio}-azetidin-1-yl]acetate (500 mg) was added. The mixture was cooled to 10° to 15° C. and zinc powder (400 mg) was added thereto with stirring and then the stirring was continued for an hour. The reaction mixture was filtered and the filtrate was diluted with ethyl acetate (20 ml), washed successively with 5% aqueous solution of sodium bicarbonate and sodium chloride, dried over magnesium sulfate and then evaporated in vacuo to give benzyl 2-triphenylphosphoranylidene-2-[2-oxo-3β-(2-phenylacetamido)-4β-(2-hydroxyacetylthio)azetidin-1-yl]acetate (0.37 g).

I. R. ($CH_2Cl_2$): 3300, 1760, 1690, 1610 $cm^{-1}$

Preparation of the object compound (b) To a mixture of dimethylsulfoxide (0.4 ml) and acetic anhydride (0.4 ml), benzyl 2-triphenylphosphoranylidene-2-[2-oxo-3β-(2-phenylacetamido)-4β-(2-hydroxyacetylthio)azetidin-1-yl]acetate (92 mg) was added and the mixture was stirred for 6.5 hours at room temperature. In the course of the reaction, benzyl 2-triphenylphosphoranylidene-2-[2-oxo-3β-(2-phenylacetamido)-4β-(glyoxyloylthio)azetidin-1-yl]-acetate was produced. The reaction mixture was concentrated in vacuo and the residue was dissolved in ethyl acetate (20 ml). The ethyl acetate layer was separated, washed successively with ice-water, 2% aqueous solution of sodium bicarbonate and water, dried over magnesium sulfate and then evaporated in vacuo. The residue was subjected to column chromatography on silica gel, using a mixture of benzene and ethyl acetate (3:1) as an eluent to give a foam of benzyl 7β-(2-phenylacetamido)-2-oxo-3-cephem-4-carboxylate (12 mg).

I. R. ($CH_2Cl_2$): 3400, 1800, 1730, 1690, 1650 $cm^{-1}$

N.M.R. ($CDCl_3,\delta$):3.60 (2H, s), 5.26 (2H, s), 5.62 (1H, d, J=4 Hz), 5.80 (1H, dd, J=4 and 8 Hz), 6.36 (1H, s), 6.60 (1H, d, J=8 Hz), 7.0–7.4 (10H, m).

EXAMPLE 5

To a solution of benzyl 7β-(2-phenoxyacetamido)-1-oxadethia-2-oxo-3-cephem-4-carboxylate (379 mg.) in methylene chloride (10 ml.) were added N,N-dimethylaniline (218 mg.) and phosphorus pentachloride (373 mg.) at −40° C. followed by stirring at about −35° C. for 50 minutes. To the mixture was added methanol (0.6 ml.) at −55° C., and the temperature was gradually raised to 0° C. over a period of 70 minutes. To the reaction mixture was added water (0.3 ml.) followed by stirring under ice-cooling for 25 minutes. The precipitates were collected by filtration, washed with a small amount of isopropyl alcohol and then dried over phosphorus pentoxide under reduced pressure to give benzyl 7β-amino-1-oxadethia-2-oxo-3-cephem-4-carboxylate.-hydrochloride (70 mg.), m.p. 70° to 82° c. (dec.).

I.R. (Nujol) 1820, 1730 $cm^{-1}$

N.M.R. ($CD_3OD,\delta$) 5.24 (1H, d, J=4 Hz), 6.15 (1H, d, J=4 Hz), 5.33 (2H, s), 6.46 (1H, s), 7.4 (5H, m)

EXAMPLE 6

To a solution of benzyl 7β-(2-phenoxyacetamido)-2-oxo-3-cephem-4-carboxylate (294 mg) in methylene chloride (7 ml) were added successively N,N-dimethylaniline (0.17 ml) and phosphorus pentachloride (281 mg) at −35° C. The mixture was stirred for 1.5 hours at −35° to −30° C. and cooled to −50° C. and then thereto was added methanol (0.57 ml). After the temperature was raised gradually to 0° C. over a period of 1.5 hours, water (0.5 ml) was added. The precipitates were collected by filtration and washed with a small amount of isopropyl alcohol to give benzyl 7β-amino-2-oxo-3-cephem-4-carboxylate hydrochloride (96.5 mg).

I.R. (Nujol): 3140, 1800, 1730, 1640 $cm^{-1}$

N.M.R. ($DMSO-d_6, \delta$): 5.40 (2H, s and 1H, d, J=5 Hz), 6.13 (1H, d, J=5 Hz), 6.45 (1H, s), 7.45 (5H,s).

EXAMPLE 7

To a solution (1 ml.) of N,N-dimethylformamide (292 mg.) in methylene chloride (10 ml.) was added a solution (1 ml.) of phosphorus oxychloride (318 mg.) in methylene chloride (10 ml.) under ice-cooling followed by stirring at the same temperature for 80 minutes. To a mixture was added 2-pentyloxyimino-2-(2-formamidothiazol-4-yl)acetic acid (syn isomer)(57 mg.), and the resulting clear solution was stirred for an hour under ice-cooling. On the other hand, a suspension of benzyl 7β-amino-1-oxadethia-2-oxo-3-cephem-4-carboxylate.-hydrochloride (50 mg.) in methylene chloride (2 ml.) was cooled to −45° C. and thereto was added a solution (1 ml.) of pyridine (400 mg.) in methylene chloride (10 ml.). To the mixture was added immediately the clear solution obtained above, and the temperature was gradually raised to −5° C. over a period of 85 minutes. After the reaction mixture was poured into a mixture of ethyl acetate (50 ml.) and cold water, the organic layer was separated. The organic layer was washed successively with cold diluted hydrochloric acid, a cold diluted aqueous solution of sodium bicarbonate and an aqueous solution of sodium chloride, dried over magnesium sulfate and then evaporated to give a yellow oil (62 mg.). Thus obtained oil was chromatographed on silica gel (1.3 g.) and eluted with a mixture of benzene and ethyl acetate (3:1). The fractions containing the desired compound were evaporated to give benzyl 7β-[2-pentyloxyimino-2-(2-formamidothiazol-4-yl)acetamido]-1-oxadethia-2-oxo-3-cephem-4-carboxylate (syn isomer) (30 mg.).

I.R. ($CH_2Cl_2$) 3350, 1810, 1730, 1690 $cm^{-1}$

N.M.R. ($CD_3COCD_3,\delta$) 0.90 (3H, t, J=6 Hz), 1.1–1.9 (6H, m) 4.17 (2H, t, J=6 Hz), 5.40 (2H, s), 5.96 (1H, dd, J=4, 8 Hz), 6.20 (1H, d, J=4 Hz), 6.34 (1H, s), 7.34 (1H, s), 7.43 (5H, m), 8.48 (1H, d, J=8 Hz), 8.67 (1H, s), 11.50 (1H, broad)

EXAMPLE 8

The following compounds were prepared in the similar manner to that described in Example 7.

(1) Benzyl 7β-(2-methoxyimino-2-phenylacetamido)-1-oxadethia-2-oxo-3-cephem-4-carboxylate (syn isomer).

I.R. (CH$_2$Cl$_2$) 3390, 1815, 1740, 1685, 1610 cm$^{-1}$
N.M.R. ((CD$_3$)$_2$C=0,δ) 3.95 (3H, s), 5.40 (2H, s), 6.03 (1H, dd, J=4,8 Hz), 6.23 (1H, d, J=4 Hz), 7.33–7.83 (10–11H, m)

(2) Benzyl 7β-(2-phenoxyacetamido)-1-oxadethia-2-oxo-3-cephem-4-carboxylate.

I.R. (CH$_2$Cl$_2$): 1820, 1745, 1700 cm$^{-1}$ (3) Benzyl 7β-benzyloxycarboxamido-1-oxadethia-2-oxo-3-cephem-4-carboxylate.

I.R. (CH$_2$Cl$_2$): 1818, 1735 cm$^{-1}$ (4) 7β-[2-Pentyloxyimino-2-(2-formamidothiazol-4-yl)-acetamido]-1-oxadethia-2-oxo-3-cephem-4-carboxylic acid (sym isomer).

I.R. (Nujol): 1800, 1720, 1680, 1660 cm$^{-1}$ (5) 7β-(2-Methoxyimino-2-phenylacetamido)-1-oxadethia-2-oxo-3-cephem-4-carboxylic acid (syn isomer).

I.R. (Nujol): 3370, 1815, 1740, 1680 cm$^{-1}$

7β-(2-Phenoxyacetamido)-1-oxadethia-2-oxo-3-cephem-4-carboxylic acid.

I.R. (CH$_2$Cl$_2$): 1815, 1735, 1695 cm$^{-1}$ (7) 7β-Benzyloxycarboxamido-1-oxadethia-2-oxo-3-cephem-4-carboxylic acid.

I.R. (CH$_2$Cl$_2$): 1815, 1730 cm$^{-1}$ (8) 7β-[2-Pentyloxyimino-2-(2-aminothiazol-4-yl)-acetamido]-1-oxoadethia-2-oxo-3-cephem-4-carboxylic acid hydrochloride (syn isomer).

I.R. (Nujol): 1800, 1720, 1660, 1620 cm$^{-1}$ (9) Benzyl 7β-(2-phenoxyacetamido)-2-oxo-3-cephem-4-carboxylate.

I.R. (CH$_2$Cl$_2$): 3390, 1805, 1735, 1700, 1655 cm$^{-1}$

(10) Benzyl 7β-(2-phenylacetamido)-2-oxo-3-cephem-4-carboxylate.

I.R. (CH$_2$Cl$_2$): 3400, 1800, 1730, 1690, 1650 cm$^{-1}$

(11) 7β-(2-Phenoxyacetamido)-2-oxo-3-cephem-4-carboxylic acid.

I.R. (Nujol): 3350, 1810, 1790, 1725, 1650 cm$^{-1}$

(12) 7β-(2-Phenylacetamido)-2-oxo-3-cephem-4-carboxylic acid.

I.R. (CH$_2$Cl$_2$): 1800, 1750, 1685, 1650 cm$^{-1}$

(13) Benzyl 7β-(2-phenoxyacetamido)-1-oxadethia-2-oxocepham-4α-carboxylate.

I.R. (Nujol): 3320, 1780, 1770, 1740, 1680 cm$^{-1}$

(14) Benzyl 7β-(2-phenoxyacetamido)-1-oxadethia-2-oxocepham-4β-carboxylate.

I.R. (Nujol): 3320, 1780, 1770, 1740, 1680 cm$^{-1}$

(15) Benzyl 7β-(2-methoxyimino-2-phenylacetamido)-1-oxadethia-2-oxocepham-4α-carboxylate (sym isomer).

I.R. (CH$_2$Cl$_2$): 3370, 1790, 1760, 1740, 1680 cm$^{-1}$

(16) Benzyl 7β-(2-methoxyimino-2-phenylacetamido)-1-oxadethia-2-oxocepham-4β-carboxylate (syn isomer).

I.R. (CH$_2$Cl$_2$): 3370, 1790, 1770, 1740, 1680 cm$^{-1}$

(17) Benzyl 7β-benzyloxycarboxamido-1-oxadethia-2-oxocepham-4α-carboxylate.

I.R. (CH$_2$Cl$_2$): 1800, 1770, 1730 cm$^{-1}$

(18) Benzyl 7β-benzyloxycarboxamido-1-oxadethia-2-oxocepham-4β-carboxylate.

I.R. (CH$_2$Cl$_2$): 1800, 1775, 1740, 1725 cm$^{-1}$

(19) 7β-(2-Phenoxyacetamido)-1-oxadethia-2-oxocepham-4α-carboxylic acid.

I.R. (Nujol): 3320, 1780, 1750, 1730, 1640 cm$^{-1}$

(20) 7β-(2-Methoxyimino-2-phenylacetamido)-1-oxadethia-2-oxocepham-4α-carboxylic acid (syn isomer).

I.R. (Nujol): 1790, 1730, 1650 cm$^{-1}$

(21) 7β-(2-Methoxyimino-2-phenylacetamido)-1-oxadethia-2-oxocepham-4β-carboxylic acid (syn isomer).

I.R. (Nujol): 3330, 1800, 1770, 1680 cm$^{-1}$

EXAMPLE 9

To a solution of benzyl 7β-(2-phenoxyacetamido)-1-oxadethia-2-oxo-3-cephem-4-carboxylate (1.16 g) in methylene chloride (14 ml) were successively added acetic acid (1.7 ml) and zinc powder (1.34 g) at room temperature. The resulting mixture was stirred for 25 minutes at room temperature. The reaction mixture was diluted with ethyl acetate and then filtered through a pad of Celite. The filtrate was successively washed with water, a dil. aqueous solution of sodium bicarbonate and an aqueous solution of sodium chloride and then dried over magnesium sulfate. Evaporation of the solution gave an amorphous solid (1.25 g), which was crystallized by addition of benzene and a small amount of methylene chloride to give benzyl 7β-(2-phenoxyacetamido)-1-oxadethia-2-oxocepham-4α-carboxylate (775 mg). mp. 130° to 136° C.

I.R. (Nujol): 3320, 1780, 1770, 1740, 1680 cm$^{-1}$
N.M.R. (CDCl$_3$,δ): 2.91 (2H, AB part of the ABX pattern J$_{AB}$=16 Hz, J$_{AX}$=10 Hz, J$_{BX}$=8 Hz), 4.50 (2H, S), 4.75 (1H, X part of the ABX pattern J$_{AX}$=10 Hz, J$_{BX}$=8 Hz), 5.20 (2H, S) 5.57 (1H, d d, J=3 and 9 Hz), 5.76 (1H, d, J=3 Hz),

| 6.84–7.10 | (10H, m), |
| 7.24–7.40 | |

7.50 (1H, d, J=9 Hz).

The mother liquor was concentrated and chromatographed on silica gel (12 g), and eluted with a mixture of benzene and ethyl acetate (7:1 and then 4:1). From the fractions of benzene and ethyl acetate (7:1), the crystals (16 mg) of the same compound were obtained.

Further, from the fractions of benzene and ethyl acetate (4:1), there was obtained an oil (89 mg), which was crystallized by addition of benzene and diethyl ether to give benzyl 7β-(2-phenoxyacetamido)-1-oxadethia-2-oxocepham-4α-carboxylate (65 mg), mp 114° to 115.5° C.

I.R. (Nujol): 3400, 1800, 1780, 1760 cm$^{-1}$
N.M.R. (CDCl$_3$,δ): 2.90 (2H, d, J=5 Hz), 4.44 (1H, d t, J=1.5 and 5 Hz), 4.50 (2H, s), 5.20 (2H,s), 5.62 (1H, d d d, J=1.5 and 3.5 and 9 Hz), 5.71 (1H, J=3.5 Hz),

| 6.84–7.12 | (10H, m). |
| 7.24–7.42 | |

EXAMPLE 10

To a solution of benzyl 7β-(2-methoxyimino-2-phenylacetamido)-1-oxadethia-2-oxo-3-cephem-4-carboxylate (syn isomer) (135 mg) in methylene chloride (4 ml) were successively added acetic acid (0.45 ml) and zinc powder (270 mg) at room temperature and then the resulting mixture was stirred for 10 minutes. The reaction mixture was diluted with ethyl acetate and filtered through Celite. The filtrate was washed successively

UNITED STATES PATENT AND TRADEMARK OFFICE
CERTIFICATE OF CORRECTION

PATENT NO. : 4,264,597
DATED : April 28, 1981
INVENTOR(S) : MASASHI HASHIMOTO ET AL It is certified that error appears in the above—identified patent and that said Letters Patent is hereby corrected as shown below:

On the title page, "32" Claims should read -- 33 Claims --.

In Col. 48, line 50, the formula should read:

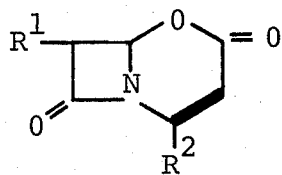

In Col. 48, line 58, "protecitve" should read --protective--

In Col. 50, line 57, add claim 33 as follows:

--33. A pharmaceutical composition comprising a compound of claim 1 or pharmaceutically acceptable salt thereof in association with a pharmaceutically acceptable, substantially non-toxic carrier or excipient.--

Signed and Sealed this

First Day of September 1981

[SEAL]

Attest:

GERALD J. MOSSINGHOFF

Attesting Officer    Commissioner of Patents and Trademarks

4. The compound of claim 3, wherein
R$^2$ is phenyl(lower)alkoxycarbonyl.

5. The compound of claim 4, which is benzyl 7β-amino-1-oxadethia-2-oxo-3-cephem-4-carboxylate or its hydrochloride.

6. The compound of claim 2, wherein R$^1$ is amino substituted with a pharmaceutically acceptable carboxylic acyl protective group for the amino substituents in cephalosporin compounds.

7. The compound of claim 6, wherein
R$^1$ is ar(lower)alkoxycarbonylamino, aryloxy(lower)alkanoylamino, ar(lower)alkanoylamino having a lower alkoxyimino or heterocyclic(lower)alkanoylamino having a lower alkoxyimino and R$^2$ is carboxy or ar(lower)alkoxycarbonyl.

8. The compound of claim 7, wherein
R$^1$ is phenyl(lower)alkoxycarbonylamino, phenoxy(lower)alkanoylamino, phenyl(lower)alkanoylamino having a lower alkoxyimino or thiazolyl(lower)alkanoylamino having a lower alkoxyimino and an amino or a lower alkanoylamino and R$^2$ is carboxy or phenyl(lower)alkoxycarbonyl.

9. Compound of claim 8, wherein
R$^1$ is benzyloxycarboxamido, phenoxyacetamido, 2-methoxyimino-2-phenylacetamido, 2-pentyloxyimino-2-(2-aminothiazol-4-yl)acetamido or 2-pentyloxyimino-2-(2-formamidothiazol-4-yl)acetamido; and
R$^2$ is carboxy or benzyloxycarbonyl.

10. The compound of claim 9, which is
7β-[2-pentyloxyimino-2-(2-aminothiazol-4-yl)-acetamido]-1-oxadethia-2-oxo-3-cephem-4-carboxylic acid (syn isomer) or its hydrochloride.

11. The compound of claim 9, which is
7β-[2-pentyloxyimino-2-(2-formamidothiazol-4-yl)acetamido]-1-oxadethia-2-oxo-3-cephem-4-carboxylic acid (syn isomer).

12. The compound of claim 9, which is
7β-(2-methoxyimino-2-phenylacetamido)-1-oxadethia-2-oxo-3-cephem-4-carboxylic acid (syn isomer).

13. The compound of claim 9, which is
7β-(2-phenoxyacetamido)-1-oxadethia-2-oxo-3-cephem-4-carboxylic acid.

14. The compound of claim 9, which is
7β-benzyloxycarboxamido-1-oxadethia-2-oxo-3-cephem-4-carboxylic acid.

15. The compound of claim 9, which is
benzyl 7β-(2-methoxyimino-2-phenylacetamido)-1-oxadethia-2-oxo-3-cephem-4-carboxylate (syn isomer).

16. The compound of claim 9, which is
benzyl 7β-[2-pentyloxyimino-2-(2-formamidothiazol-4-yl)acetamido]-1-oxadethia-2-oxo-3-cephem-4-carboxylate (syn isomer).

17. The compound of claim 9, which is
benzyl 7β-(2-pheoxyacetamido)-1-oxadethia-2-oxo-3-cephem-4-carboxylate.

18. The compound of claim 9, which is
benzyl 7β-benzyloxycarboxamido-1-oxadethia-2-oxo-3-cephem-4-carboxylate.

19. The compound of claim 1, wherein
the heavy solid line means single bond.

20. The compound of claim 19, wherein R$^1$ is amino substituted with a pharmaceutically acceptable carboxylic acyl protective group for the amino substituents in cephalosporin compounds.

21. The compound of claim 20, wherein
R$^1$ is ar(lower)alkoxycarbonylamino, aryloxy(lower)alkanoylamino or ar(lower)alkanoylamino having a lower alkoxyimino; and
R$^2$ is carboxy or ar(lower)alkoxycarbonyl.

22. The compound of claim 21, wherein
R$^1$ is phenyl(lower)alkoxycarbonylamino, phenoxy(lower)alkanoylamino or phenyl(lower)alkanoylamino having a lower alkoxyimino; and
R$^2$ is carboxy or phenyl(lower)alkoxycarbonyl.

23. The compound of claim 22, wherein
R$^1$ is benzyloxycarboxamido, phenoxyacetamido or 2-methoxyimino-2-phenylacetamido; and
R$^2$ is carboxy or benzyloxycarbonyl.

24. The compound of claim 23, which is
7β-(2-phenoxyacetamido)-1-oxadethia-2-oxocepham-4α-carboxylic acid.

25. The compound of claim 23, which is
7β-(2-methoxyimino-2-phenylacetamido)-1-oxadethia-2-oxocepham-4α-carboxylic acid (syn isomer).

26. The compound of claim 23, which is
7β-(2-methoxyimino-2-phenylacetamido)-1-oxadethia-2-oxocepham-4β-carboxylic acid (syn isomer).

27. The compound of claim 23, which is
benzyl 7β-(2-phenoxyacetamido)-1-oxadethia-2-oxocepham-4α-carboxylate.

28. The compound of claim 23, which is
benzyl 7β-(2-phenoxyacetamido)-1-oxadethia-2-oxocepham-4β-carboxylate.

29. The compound of claim 23, which is
benzyl 7β-(2-methoxyimino-2-phenylacetamido)-1-oxadethia-2-oxocepham-4α-carboxylate (syn isomer).

30. The compound of claim 23, which is
benzyl 7β-(2-methoxyimino-2-phenylacetamido)-1-oxadethia-2-oxocepham-4β-carboxylate (syn isomer).

31. The compound of claim 23, which is
benzyl 7β-benzyloxycarboxamido-1-oxadethia-2-oxocepham-4α-carboxylate.

32. The compound of claim 23, which is
benzyl 7β-benzyloxycarboxamido-1-oxadethia-2-oxocepham-4β-carboxylate.

* * * * *

UNITED STATES PATENT AND TRADEMARK OFFICE
CERTIFICATE OF CORRECTION

PATENT NO. : 4,264,597
DATED : April 28, 1981
INVENTOR(S) : MASASHI HASHIMOTO ET AL It is certified that error appears in the above—identified patent and that said Letters Patent is hereby corrected as shown below:

On the title page, "32" Claims should read -- 33 Claims --.

In Col. 48, line 50, the formula should read:

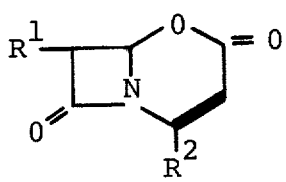

In Col. 48, line 58, "protecitve" should read --protective--

In Col. 50, line 57, add claim 33 as follows:

--33. A pharmaceutical composition comprising a compound of claim 1 or pharmaceutically acceptable salt thereof in association with a pharmaceutically acceptable, substantially non-toxic carrier or excipient.--

Signed and Sealed this

First Day of September 1981

[SEAL]

Attest:

GERALD J. MOSSINGHOFF

Attesting Officer   Commissioner of Patents and Trademarks